US011369600B2

(12) United States Patent
Nguyen et al.

(10) Patent No.: US 11,369,600 B2
(45) Date of Patent: *Jun. 28, 2022

(54) OPHTHALMIC FORMULATIONS OF TYROSINE KINASE INHIBITORS, METHODS OF USE THEREOF, AND PREPARATION METHODS THEREOF

(71) Applicant: Allgenesis Biotherapeutics Inc., Taipei (TW)

(72) Inventors: Tan Nguyen, Fullerton, CA (US); Chin-Yu Lai, Taipei (TW)

(73) Assignee: ALLGENESIS BIOTHERAPEUTICS INC., Taipei (TW)

( * ) Notice: Subject to any disclaimer, the term of this patent is extended or adjusted under 35 U.S.C. 154(b) by 25 days.

This patent is subject to a terminal disclaimer.

(21) Appl. No.: 15/964,235

(22) Filed: Apr. 27, 2018

(65) Prior Publication Data

US 2018/0243294 A1    Aug. 30, 2018

Related U.S. Application Data

(63) Continuation of application No. 15/700,735, filed on Sep. 11, 2017, now Pat. No. 10,154,994, which is a continuation of application No. PCT/US2016/034822, filed on May 27, 2016.

(60) Provisional application No. 62/183,180, filed on Jun. 22, 2015.

(51) Int. Cl.
| | |
|---|---|
| *A61K 31/496* | (2006.01) |
| *A61K 31/506* | (2006.01) |
| *A61K 9/00* | (2006.01) |
| *A61K 31/44* | (2006.01) |
| *A61K 31/4439* | (2006.01) |
| *A61K 9/51* | (2006.01) |
| *A61K 47/38* | (2006.01) |
| *A61K 9/10* | (2006.01) |
| *A61K 9/14* | (2006.01) |

(52) U.S. Cl.
CPC .......... *A61K 31/496* (2013.01); *A61K 9/0048* (2013.01); *A61K 9/10* (2013.01); *A61K 9/146* (2013.01); *A61K 9/5146* (2013.01); *A61K 31/44* (2013.01); *A61K 31/4439* (2013.01); *A61K 31/506* (2013.01); *A61K 47/38* (2013.01)

(58) Field of Classification Search
None
See application file for complete search history.

(56) References Cited

U.S. PATENT DOCUMENTS

| | | | |
|---|---|---|---|
| 6,071,904 A | 6/2000 | Ali et al. | |
| 7,846,936 B2 | 12/2010 | Hilberg et al. | |
| 8,686,023 B2 | 4/2014 | Selic | |
| 8,747,852 B1 | 6/2014 | Pham | |
| 9,980,901 B2 | 5/2018 | Ni | |
| 9,987,223 B2 | 6/2018 | Ni | |
| 2008/0003219 A1 | 1/2008 | Peyman | |
| 2008/0254040 A1 | 10/2008 | Stefanic et al. | |
| 2011/0142923 A1 | 6/2011 | Mazzone et al. | |
| 2013/0316006 A1 | 11/2013 | Popov et al. | |
| 2014/0186336 A1 | 7/2014 | Pham | |
| 2014/0235678 A1* | 8/2014 | Bottger | A61K 9/0048 514/350 |
| 2015/0037422 A1 | 2/2015 | Kaplan et al. | |
| 2015/0141448 A1 | 5/2015 | Böttger et al. | |
| 2015/0164790 A1 | 6/2015 | Böttger et al. | |
| 2015/0174096 A1 | 6/2015 | Böttger et al. | |
| 2016/0038760 A1 | 2/2016 | Hamrah et al. | |
| 2017/0172915 A1* | 6/2017 | Ni | A61P 27/00 |
| 2017/0209368 A1 | 7/2017 | Ni | |

FOREIGN PATENT DOCUMENTS

| | | | |
|---|---|---|---|
| RU | 2 351 298 C1 | 4/2009 | |
| WO | 2007/038453 A2 | 4/2007 | |
| WO | 2013/188283 A1 | 12/2013 | |
| WO | 2014/074823 A1 | 5/2014 | |
| WO | 2016/200688 A1 | 12/2016 | |
| WO | 2016/209555 A1 | 12/2016 | |
| WO | WO-2016200688 A1 * | 12/2016 | ............. A61K 47/26 |

OTHER PUBLICATIONS

Huu, Journal of Controlled Release, 200, 2015 (Year: 2015).*
Macugen, European Medicines Agency, 2012 (Year: 2012).*
U.S. Appl. No. 15/700,735, "Final Office Action", dated Apr. 10, 2018.
U.S. Appl. No. 15/700,735, "Non-Final Office Action", dated Nov. 17, 2017.
U.S. Appl. No. 15/474,620, "U.S. Application No.", Third Party Submission Under C.F.R. §1.290, Oct. 20, 2017.
Al-Torbak, "Photodynamic Therapy with Verteporfin for Corneal Neovascularization", Middle East African Journal of Ophthalmology, vol. 19, No. 2, Apr.-Jun. 2012, pp. 185-189.
Amparo et al., "Safety and Efficacy of the Multi targeted Receptor Kinase Inhibitor Pazopanib in the Treatment of Corneal Neovascularization", Investigative Ophthalmology & Visual Science, vol. 54, No. 1, Jan. 2013, pp. 537-544.
Assessment Report, International non-proprietary name: nintedanib, EMA/76777/2015, European Medicines Agency, Nov. 20, 2014.
"Australian Public Assessment Report for Pazopanib Hydrochloride", Australian Government Dept. of Health and Ageing Therapeutic Goods Administration, Available online at: www.tga.gov.au/sites/default/files/auspar-votrient.pdf, Sep. 2010, 104 pages.
"Australian Public Assessment Report for Vandetanib", Australian Government Dept. of Health and Ageing Therapeutic Goods Administration, Available online at: www.tga.gov.au/sites/default/files/auspar-vandetanib-130807.pdf, Aug. 2013, 73 pages.

(Continued)

*Primary Examiner* — Robert A Wax
*Assistant Examiner* — William Craigo
(74) *Attorney, Agent, or Firm* — Kilpatrick Townsend & Stockton LLP

(57) ABSTRACT

Ophthalmic formulations containing nintedanib, or a pharmaceutically acceptable salt thereof are provided. The ophthalmic formulations can contain microparticles or nanoparticles of nintedanib. Also provided are methods of using the ophthalmic formulations for treating ocular surface diseases, such as dry eye disease.

15 Claims, 3 Drawing Sheets

(56) References Cited

OTHER PUBLICATIONS

Barot et al., "Prodrug Strategies in Ocular Drug Delivery", Med Chem., vol. 8, No. 4, 2012, pp. 753-768.
Bayyoud et al., "Cytotoxic Properties of Sunitinib and Sorafenib on Human Corneal Epithelial Cells", Current Eye Research, vol. 39, No. 2, 2014, pp. 149-154.
Campos-Mollo et al., "New Comeal Neovascularization Model in Rabbits for Angiogenesis Research", Ophthalmic Res., 2011, vol. 45, pp. 135-141.
"Caprelsa® (Vandetanib) FDA Label", Available online at: www.accessdata.fda.gov/drugsatfdadocs/label/2014/022405s0071b1.pdf., Mar. 2014, 21 pages.
"Clinical Pharmacology and Biopharmaceutics Review for Inlyta® (Axitinib)", Application No. 2023240rig1s000, 17 Center for Drug Evaluation and Research, U.S. Food and Dmg Administration, Available online at: www.accessdata.fda.gov/drugsatfda_docs/nda/2012/2023240rig1sOOOClinPharrnR.pdf., Feb. 27, 2012, 119 pages.
"Clinical Pharmacology and Biopharmaceutics Review for (OFEV) Nintedanib Capsules", 2058320rig1s000, Center for Drug Evaluation and Research, U.S. Food and Dmg Administration, Available online at: www.accessdata.fda.gov/drugsatfda_docs/nda/2014/2058320rig1s000ClinPharmR.pdf., Nov. 1, 2014, 141 pages.
"Clinical Pharmacology and Biopharmaceutics Review for Tarceva™ (Erlotinib hydrochloride)", Application No. 21-743, Center for Drug Evaluation and Research, U.S. Food and Drug Administration, Available online at: www.accessdata.fda.gov/dmgsatfda docs/nda/2004/21-743_Tarceva biopharrnr.PDF, Mar. 28, 2005, 88 pages.
Cox et al., "Doxycycline's Effect on Ocular Angiogenesis: an In Vivo Analysis", Ophthalmology, vol. 117, No. 9, Sep. 2010, pp. 1782-1791.
Davis et al., "Comprehensive Analysis of Kinase Inhibitor Selectivity", Nature Biotechnology, vol. 29, No. 11, Nov. 2011, pp. 1046-1052.
Fossarello et al., "Photodynamic Therapy of Corneal Neovascularization with Verteporfin", Cornea, vol. 22, No. 5, Jul. 1, 2003, pp. 485-488.
Fossarello et al., "Photodynamic Therapy of Pterygium with Verteporfin: A Preliminary Report", Cornea, vol. 23, No. 4, May 2004, pp. 330-338.
Gougis et al., "Clinical Pharmacology of Anti-Angiogenic Drugs in Oncology", Critical Reviews in Oncology/Hematology, vol. 119, 2017, pp. 75-93.
Hall et al., "Angiogenesis Inhibition as a Therapeutic Strategy in Non-Small Cell Lung Cancer (NSCLC)", Translational Lung Cancer Research, vol. 4, No. 5, Oct. 2015, pp. 515-523.
Hilberg et al., "BIBF 1120: Triple Angiokinase Inhibitor with Sustained Receptor Blockade and Good Antitumor Efficacy", Cancer Research, vol. 68, No. 12, Jun. 15, 2008, pp. 4774-4782.
Hueber et al., "Photodynamic Therapy for Wound-Healing Modulation in Pterygium Surgery. A Clinical Pilot Study", Graefe's Arch Clin Exp Opthalmol, vol. 243, Apr. 2005, pp. 942-946.
Huu, "Light-Responsive Nanoparticle Depot to Control Release of a Small Molecule Angiogenesis Inhibitor in the Posterior Segment of the Eye", Journal of Controlled Release, vol. 200, Feb. 28, 2015, pp. 71-77.
Jain et al., "Population Pharmacokinetic Analysis of Sorafenib in Patients with Solid Tumours", Br. J. Clin Pharmacal., vol. 72, No. 2, 2011, pp. 294-305.
Jovanovic et al., "The Effect of Topical Doxycycline on Corneal Neovascularization", Current Eye Research, vol. 39, No. 2,, Feb. 1, 2014, pp. 142-148.
Kareem et al., "The Use of Antimetabolites as Adjunctive Therapy in the Surgical Treatment of Pterygium", Clinical Ophthalmology, vol. 6, Nov. 7, 2012, pp. 1849-1854.
Ko et al., "Inhibition of Corneal Neovascularization by Subcolliunctival and Topical Bevacizumab and Sunitinib in a Rabbit Model", Cornea, vol. 32, No. 5, May 2013, pp. 689-695.
Kumar et al., "Myelosuppression and Kinase Selectivity of Multikinase Angiogenesis Inhibitors", British Journal of Cancer, vol. 101, Oct. 2009, pp. 1717-1723.
Lachman et al., "The Theory and Practice of Industial Pharmacy", Journ. Of Pharma. Sciences, vol. 59, No. 10, 1986, pp. 1531-1532.
Lee et al., "Effect of Porcine Chondrocyte-Derived Extracellular Matrix on the Pterygium in Mouse Model", Graefes Arch ClinExp Ophthalmol, vol. 252, No. 4, Apr. 2014, pp. 609-618.
Maddula, "Horizons in Therapy for Corneal Angiogenesis", Ophthalmology, vol. 118, No. 3, Mar. 2011, pp. 591-599.
Manallack et al., "The Significance of Acid/Base Properties in Drug Discovery", Chemical Society Reviews, vol. 42, No. 2, Jan. 21, 2013, pp. 485-496.
"Nexavar European Public Assessment Report (EPAR)—Scientific Discussion", European Medicines Agency, Available online at: http://www.ema.europa.eu/docs/en_GB/document_library/EPAR_-Scientific_Discussionlhuman/000690/WC500027707.pdf, Apr. 3, 2007, 51 pages.
PCT/US2016/035726, "International Report on Patentability in International Application", dated Dec. 21, 2017.
PCT/US2016/035726, "International Search Report and Written Opinion", dated Sep. 1, 2016.
PCT/US2016/34822, "International Search Report and Written Opinion", dated Aug. 23, 2016.
Perez-Santonja et al., "Inhibition of Corneal Neovascularization by Topical Bevacizumab (Anti-VEGF) and Sunitinib (Anti-VEGF and Anti PDGF) in an Animal Model", Am J Ophthalmol., vol. 150, No. 4, Oct. 2010, pp. 519-528.
Rautio et al, "Prodrugs: Design and Clinical Applications", Nature Reviews, vol. 7, 2008, pp. 255-270.
Roskoski, "Sunitinib: A VEGF and PDGF Receptor Protein Kinase and Angiogenesis Inhibitor", Biochem. Biophys. Res. Comm., vol. 356, 2007, pp. 323-328.
Roth et al., "Nintedanib: From Discovery to the Clinic", J. Med. Chem., vol. 58, 2015, pp. 1053-1063.
Rua et al., "Oral Doxycycline Reduces Pterygium Lesions: Results from a Double Blind, Randomized, Placebo Controlled Clinical Trial", PLOS One, vol. 7, No. 12, e52696,, Dec. 2012, 7 pages.
Sangwan et al., "Novel Salts of Sunitinib an Anticancer Drug with Improved Solubility", Int'l Res. J. of Pure and Applied Chem., vol. 5, No. 4,, 2015, pp. 352-365.
Seo et al., "Inhibition of Corneal Neovascularization in Rats by Systemic Administration of Sorafenib", Cornea, vol. 31, No. 8, 2012, pp. 907-912.
Sun et al., "Discovery of 5-[5-Fluoro-2-oxo-1,2-dihydroindol-(3Z)-ylidenemethyl]-2,4-dimehtyl-1H-pyrrol-3-carboxylic Acid (2-Diethylaminoethylamide", A Novel Tyrosine Kinase Inhibitor Targeting Vascular Endothelial and Platelet-Derived Growth Factor Receptor Tyrosine Kinase, J Med Chem, vol. 46, No. 7,, 2003, pp. 1116-1119.
"Sutent European Public Assessment Report (EPAR)—Scientific Discussion, European Medicines Agency", Available online at: www.ema.europa.eu/docs/en_GB/document_library/EPAR-Scientific_Discussion/human/000687 /WC500057733.pdf., Oct. 1, 2007, 49 pages.
Truong et al., "Development of Solid Self-Emulsifying Formulation for Improving the Oral Bioavailability of Erlotinib", AAPS PharmSciTech, vol. 17, No. 2,, Apr. 2016, pp. 466-473.
WC500182476, European Medicines Agency, Nov. 20, 2014.
Wollin et al., Mode of Action of Nintedanib in the Treatment of Idiopathic Pulmonary Fibrosis:, European Respirator Journ, vol. 45, Mar. 5, 2015, pp. 1434-1445.
Wu et al., "Physical and Chemical Stability of Drug Nanoparticles", Advanced Drug Delivery Reviews, vol. 63, No. 6, May 30, 2011, pp. 456-469.
Huu Viet Anh Nguyen et al, "Light-responsive nanoparticle depot to control release of a small molecule angiogenesis inhibitor in the posterior segment of the eye", Journal of Controlled Release, (Jan. 5, 2015), vol. 200, p. 71-77. DOI: http://dx.doi.org/10.1016/j.jconrel.2015.01.001.

(56) References Cited

OTHER PUBLICATIONS

Wollin, L et al., "Mode of Action of Nintedanib in the Treatment of Idiopathic Pulmonary Fibrosis.", European Respiratory Journal., (Mar. 5, 2015), vol. 45, No. 5, p. 1435-1445. *DOI: http://dx.doi.org/10.1183/09031936.00174914.

* cited by examiner

Day 7

Day 14

Day 7

Day 14

Day 7

Day 14

Day 7

Day 14

Day 7

Day 14

OPHTHALMIC FORMULATIONS OF TYROSINE KINASE INHIBITORS, METHODS OF USE THEREOF, AND PREPARATION METHODS THEREOF

CROSS REFERENCE TO RELATED APPLICATION

This application is a continuation of U.S. patent application Ser. No. 15/700,735, filed Sep. 11, 2017, which is a continuation of International Application No. PCT/US2016/034822, filed May 27, 2016, which was published in the English language on Dec. 29, 2016 under International Publication No. WO 2016/209555 A1, which is entitled to priority pursuant to 35 U.S.C. § 119(e) to U.S. Provisional Application No. 62/183,180, filed Jun. 22, 2015, and the disclosures of which are herein incorporated by reference in their entirety.

FIELD OF THE INVENTION

The invention relates to ophthalmic formulations comprising tyrosine kinase inhibitors, such as Nintedanib, Axitinib, and Sorafenib, and the use of such ophthalmic formulations for the treatment of ocular surface diseases.

BACKGROUND OF THE INVENTION

Ophthalmic medication is usually applied to the eye to treat the outside of the eye, as well as to provide intraocular treatment through the cornea. Typically, most ocular diseases are treated by topical drug application in the form of solutions, suspensions, and gels. A topical drug delivery system for ophthalmic uses should possess certain desirable properties, such as good corneal and conjunctival penetration of the active drug, prolonged pre-corneal residence time, easy instillation, non-irritating, and comfortable to minimize lachrymation and reflex blinking. It should also have appropriate rheological properties.

However, conventional dosage forms for ophthalmic applications suffer from the problems of poor ocular bioavailability due to various anatomical and pathophysiological barriers in the eye. Also, many compounds considered potentially useful in treating ocular neovascularization and disorders related to vascular permeability are often poorly soluble in water. Conventional approaches often attempt to solubilize insoluble drugs with the use of high concentrations of co-solvents, but this poses problems of toxicity and ocular tolerability.

Moreover, for certain ophthalmological conditions, an effective topical therapeutic has yet to be developed. For example, the only currently approved method to treat pterygium is surgery. Pterygium is a fleshy lesion or growth originating from the conjunctiva of the eye. Because surgery is invasive to the patient and patients are typically asymptomatic until the lesion encroaches into the cornea and blurs vision, patients are often required to live with the lesion on their eye until vision is impaired and surgery becomes necessary. Additionally, there is a high chance of recurrence of the lesion following surgery, which requires additional surgeries to remove the recurrent lesions.

Recently, tyrosine kinase inhibitors, such as Axitinib, Pazopanib, and Sorafenib have been used for ophthalmological applications. Compositions suitable for topical application to the eye containing such compounds as a therapeutically active ingredient are disclosed in U.S. Patent Application Publication No. 2015/0164790; U.S. Patent Application Publication No. 2014/0235678; U.S. Patent Application Publication No. 2011/0142923; and U.S. Patent Application Publication No. 2015/0141448. See also PCT Patent Application Publication WO 2014/074823, which discloses injectable compositions for administration to the suprachoroidal space (SCS) of the eye for treating posterior ocular disorders and choroidal maladies; and Seo et al. "Inhibition of Corneal Neovascularization in Rats by Systemic Administration of Sorafenib" *Cornea* (2012) 31(8), 907, which evaluates the effects of orally administered sorafenib on corneal neovascularization in rat models.

Despite the progress described in the art of ophthalmological formulations, there is a need in the art for improved formulations and treatment methods of ophthalmic disorders, and particularly for those disorders for which there is no non-invasive conventional alternative, such as pterygium. The formulation for ophthalmological applications should be capable of being easily administered without causing eye irritation, thus increasing patient compliance. The formulation should also deliver an active agent to the eye at a concentration which is sufficient for effective therapy.

BRIEF SUMMARY OF THE INVENTION

The invention satisfies this need by providing novel ophthalmic formulations that are efficacious in treating ocular diseases, particularly ocular surface diseases, such as pterygium. The ophthalmic formulations of the invention can be administered topically, are well tolerated, and have little to no toxicity.

In one general aspect, the invention relates to an ophthalmic formulation comprising a therapeutically effective amount of Nintedanib, a prodrug thereof, or a pharmaceutically acceptable salt thereof, and at least one pharmaceutically acceptable excipient.

In an embodiment of the invention, the ophthalmic formulation comprises Nintedanib.

In an embodiment of the invention, the ophthalmic formulation comprises Nintedanib Ethanesulfonate.

In an embodiment of the invention, the ophthalmic formulation further comprises tyloxapol as a surfactant.

In an embodiment of the invention, the ophthalmic formulation is a liquid suspension.

In an embodiment of the invention, the ophthalmic formulation is a topical ocular composition.

In particular embodiments of the invention, the ophthalmic formulation comprises a therapeutically effective amount of micronized or nanonized particles of a tyrosine kinase inhibitor selected from the group consisting of Axitinib, Nintedanib, Sorafenib, Pazopanib, a pharmaceutically acceptable prodrug thereof, and a pharmaceutically acceptable salt thereof, and at least one pharmaceutically acceptable excipient.

In a preferred embodiment of the invention, the ophthalmic formulation comprises nanonized particles of Nintedanib or a pharmaceutically acceptable salt thereof.

In another general aspect, the invention relates to a method of treating an ocular surface disease in a subject in need thereof, the method comprising administering to an eye of the subject an ophthalmic formulation of the invention.

In an embodiment of the invention, the ocular surface disease is hyperemia associated with pterygium, pterygium conjunctivae, or recurrent pterygium.

In a preferred embodiment of the invention, administration of the ophthalmic formulation is topical ocular administration.

And in yet another general aspect, the invention relates to a method of preparing an ophthalmic formulation of the invention, comprising combining a tyrosine kinase inhibitor selected from the group consisting of Axitinib, Nintedanib, Sorafenib, Pazopanib, a pharmaceutically acceptable prodrug thereof, and pharmaceutically acceptable salt thereof with at least one pharmaceutically acceptable excipient, and preferably the method further comprises forming microparticles or nanoparticles of the tyrosine kinase inhibitor for inclusion in the ophthalmic formulation of the invention.

The invention also relates to use of an ophthalmic formulation of the invention in the preparation of a medicament for treating an ocular surface disease.

BRIEF DESCRIPTION OF THE DRAWINGS

The foregoing summary, as well as the following detailed description of the invention, will be better understood when read in conjunction with the appended drawings. It should be understood that the invention is not limited to the precise embodiments shown in the drawings.

In the drawings:

FIG. 1A shows minimal neovascularization on day 7; FIG. 1B shows neovascularization of the cornea on day 14 with the arrow pointing to the area of neovascularization;

FIGS. 2A and 2B show little to no neovascularization of the cornea on day 7 and 14, respectively; the arrow in FIG. 2B points to the area of the eye in which any neovascularization would be expected to be observed;

FIGS. 3A and 3B show no neovascularization of the cornea on day 7 and 14, respectively;

FIGS. 4A and 4B show no neovascularization of the cornea on day 7 and 14, respectively;

FIGS. 5A and 5B show little neovascularization of the cornea on day 7 and 14, respectively, with the arrow pointing to the area of neovascularization.

DETAILED DESCRIPTION OF THE INVENTION

Figure 1A:
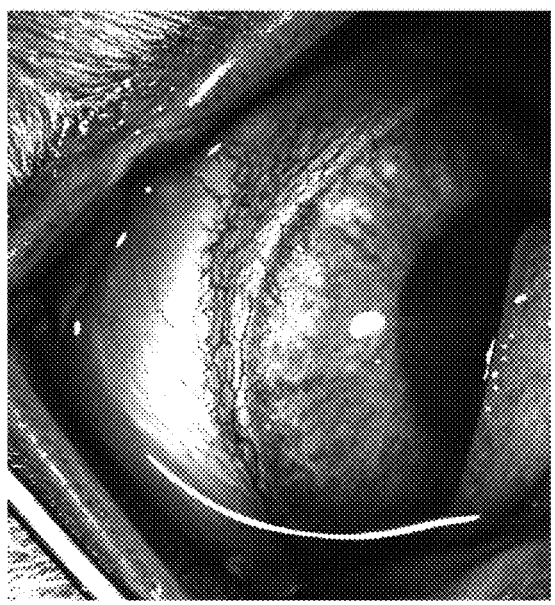
FIGS. 1A and 1B show representative photographic images of corneal neovascularization in a New Zealand white rabbit model of cornea suture-induced neovascularization upon treatment with suspension vehicle administered three times daily (TID) for a duration of 14 days.

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning commonly understood to one of ordinary skill in the art to which this invention pertains. Otherwise, certain terms used herein have the meanings as set in the specification. All patents, published patent applications and publications cited herein are incorporated by reference as if set forth fully herein. It must be noted that as used herein and in the appended claims, the singular forms "a," "an," and "the" include plural reference unless the context clearly dictates otherwise.

The phrase "pharmaceutically acceptable salt" as used herein means those salts of a compound of interest that are safe and effective for administration to a mammal and that possess the desired biological activity. Pharmaceutically acceptable acid salts include, but are not limited to hydrochloride, hydrobromide, hydroiodide, nitrate, sulfate, bisulfate, phosphate, acid phosphate, isonicotinate, carbonate, bicarbonate, acetate, lactate, salicylate, citrate, tartrate, propionate, butyrate, pyruvate, oxalate, malonate, pantothenate, bitartarte, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Suitable base salts include, but are not limited to, aluminum, calcium, lithium, magnesium, potassium, sodium, zinc, bismuth, and diethanolamine salts. For a review of pharmaceutically acceptable salts see Berge et al., *J. Pharm. Sci.* (1977) 66, 1-19, incorporated herein by reference.

The invention relates to ophthalmic formulations and methods of using the ophthalmic formulations to treat ocular surface disorders. An "ophthalmic formulation" as used herein refers to any pharmaceutical composition suitable for ocular administration, i.e., administration to the eye. Preferably, the ophthalmic formulation is suitable for topical administration to the eye, although the ophthalmic formulation can be formulated as a composition for other routes of administration such as intravitreous injection or subconjunctival injection. As illustrative and non-limiting examples, ophthalmic formulations suitable for topical administration can be in the form of a liquid, such as a suspension or a solution; cream; ointment; gel; gel-forming liquid; suspension containing liposomes or micelles; spray formulation; emulsion; erodible or non-erodible carriers that can be inserted into the cul-de-sac of the eye. In a preferred embodiment of the invention, the ophthalmic formulation is a liquid suspension.

According to embodiments of the invention, an ophthalmic formulation comprises a therapeutically effective amount of a tyrosine kinase inhibitor. The term "therapeutically effective amount" means an amount of a therapeutically active compound needed to elicit the desired biological or clinical effect. According to embodiments of the invention, "a therapeutically effective amount" is the amount of a tyrosine kinase inhibitor needed to treat an ophthalmic disorder or condition, such as an ocular surface disease.

The term "tyrosine kinase inhibitor (TKi)" as used herein refers to a therapeutically active compound that is capable of inhibiting the activity of one or more tyrosine kinases, such as, for example, platelet-derived growth factor receptor (PDGFR), fibroblast growth factor receptor (FGFR), vascular endothelial growth factor receptor (VEGFR), and Fms-like tyrosine kinase-3 (FLT3). Examples of tyrosine kinase inhibitors suitable for use with the invention include, but are not limited to, Nintedanib, Sorafenib, Axitinib, Pazopanib, pharmaceutically acceptable prodrugs thereof, and pharmaceutically acceptable salts thereof. Preferably, the tyrosine kinase inhibitor is Nintedanib or Axitinib, and more preferably is Nintedanib. Preferred pharmaceutically acceptable salts of Nintedanib include Nintedanib ethanesulfonate. Nintedanib, Sorafenib, Axitinib, and Pazopanib have the following formula (I) (II), (III), and (IV) respectively:

(I)

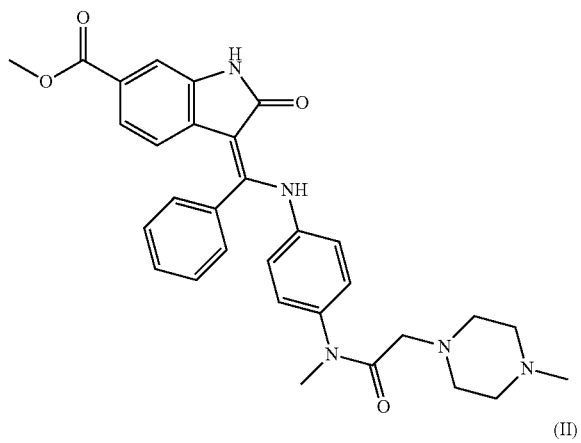

(II)

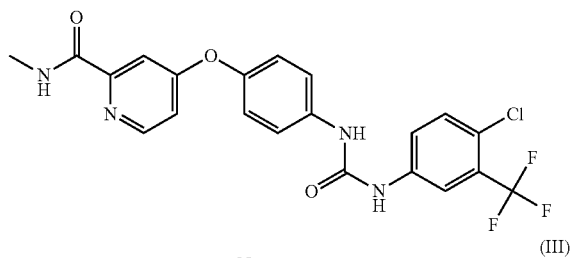

(III)

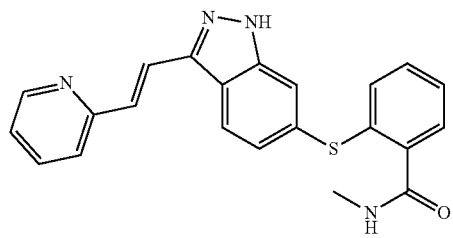

(IV)

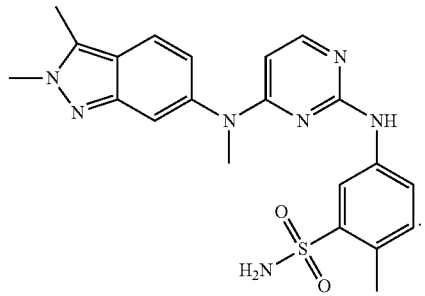

Prodrugs of the above mentioned tyrosine kinase inhibitors are also contemplated herein. The term "prodrug" as used herein means a compound that is converted in vivo to yield a compound of Formula (I), (II), (III), or (IV), or a pharmaceutically acceptable salt thereof. A prodrug is typically a drug precursor that is converted in vivo to a biologically active compound or drug. The in vivo conversion can occur by various mechanisms, including metabolic and/or chemical processes, such as, for example, through hydrolysis in the blood or target tissue, such as the eyes (see, e.g., Rautio et al., *Nature Reviews* 7, 255-270 (2008)). A discussion of the use of prodrugs is also provided by T. Higuchi and W. Stella, "Pro-drugs as Novel Delivery Systems," Vol. 41 of the A.C.S. Symposium Series; Bioreversible Carriers in Drug Design, ed. Edward B. Roche, American Pharmaceutical Association and Pergamon Press, 1987; and M Barot et al., "ProDrug Strategies in Ocular Drug Delivery" Med Chem, 8(4): 753-768, 2012.

As illustrative examples of prodrugs in accordance with embodiments of the invention, if a compound of Formula (I), (II), (III), or (IV) incorporates an amine functional group, a prodrug can be formed by replacing a hydrogen atom of the amine, urea or amide group with a functional group such as, for example, —C(O)R or —C(O)OR; or a prodrug can be formed by replacing one or two hydrogen atom(s) of a sulfonamide group with one to two functional group(s), such as —C(O)R or —RR', wherein R and R' are each independently $(C_1$-$C_{10})$alkyl, $(C_3$-$C_7)$cycloalkyl, or benzyl. Alternatively, —C(O)R can be a natural α-aminoacyl or —C(OH)C(O)OY$^1$, wherein Y$^1$ is H, $(C_1$-$C_6)$alkyl, benzyl, or —C(OY$^2$)Y$^3$; Y$^2$ is $(C_1$-$C_4)$alkyl; Y$^3$ is $(C_1$-$C_6)$ alkyl, carboxy$(C_1$-$C_6)$alkyl, amino$(C_1$-$C_4)$alkyl, mono-N— or di-N, N—$(C_1$-$C_6)$alkylaminoalkyl, or —C(Y$^4$)Y$^5$; Y$^4$ is H or methyl; and Y$^5$ is mono-N— or di-N, N—$(C_1$-$C_6)$alkylamino morpholino, piperidin-1-yl, or pyrrolidin-1-yl, and the like.

The tyrosine kinases FGFR, PDGFR, and VEGFR have been implicated in idiopathothic pulmonary fibrosis. Nintedanib Ethanesulfonate was previously approved for the treatment of idiopathic pulmonary fibrosis, as well as for treating locally advanced, metastatic or locally recurrent non-small cell lung cancer (NSCLC) in combination with docetaxel. Nintedanib has thus previously been used for oncology treatment, and to the best of the knowledge of the inventors, there is no ophthalmic drug containing Nintedanib on the market or in clinical trials.

In one embodiment of the invention, the tyrosine kinase inhibitor is Nintedanib, a prodrug thereof, or a pharmaceutically acceptable salt thereof, such as Nintedanib Ethanesulfonate.

In another embodiment of the invention, the tyrosine kinase inhibitor is Axitinib, a prodrug thereof, or a pharmaceutically acceptable salt thereof.

In another embodiment of the invention, the tyrosine kinase inhibitor is Sorafenib, a prodrug thereof, or a pharmaceutically acceptable salt thereof.

In another embodiment of the invention, the tyrosine kinase inhibitor is Pazopanib, a pharmaceutically acceptable salt thereof, or a prodrug thereof.

According to embodiments of the invention, an ophthalmic formulation comprises at least one pharmaceutically acceptable excipient. Examples of pharmaceutically acceptable excipients that can be used include, but are not limited to, surfactants, preservatives, viscosity regulators, pH-active components (e.g., pH-adjusting agents, buffering agents etc.), stabilizers, and osmo-regulators (tonicity adjusters).

Suitable surfactants that can be used in an ophthalmic formulation according to the invention include, but are not limited to, non-ionic surfactants such as poloxamers, polyoxyethylene fatty acid glycerides and oils, polyoxyethylene alkyl ethers, polyoxyethylene fatty acid esters, sorbitan esters, polyoxyethylene sorbitan esters, propylene glycol fatty acid esters, fatty acids, glyceryl fatty acid esters, α-tocopheryl polyethylene glycol succinate (TPGS), polyethoxy alkylaryl ether polymers, polymers of alkyl aryl polyether alcohol and the like. Preferably, the surfactant is Tween 80, Tween 20, poloxamer 188, poloxamer 407 or tyloxapol.

In a preferred embodiment of the invention, an ophthalmic formulation further comprises tyloxapol as a surfactant.

Suitable viscosity regulators that can be used in an ophthalmic formulation according to the invention include, but are not limited to, hydroxypropyl methylcellulose (HPMC), hydroxypropylcellulose (HPC), carboxymethylcellulose (CMC), methylcellulose (MC), hydroxyethylcellulose (HEC), cellulose and derivatives thereof, polycarbophil, polyoxyethylene glycol (PEG), hyaluronic acid (HA), amylase and derivatives thereof, amylopectins and derivatives thereof, dextran and derivatives thereof, polyvinylpyrrolidone (PVP), polyvinyl alcohol (PVA), and acrylic polymers such as derivatives of polyacrylic or polymethacrylic acid including hydroxylmethyl methacrylate (HEMA), carbomer or a mixture thereof.

In a preferred embodiment, the viscosity regulator is selected from the group consisting of HPMC, sodium carboxymethylcellulose, carbomer, polycarbophil, PEG, and HA.

In a more preferred embodiment, the viscosity regulator is HPMC.

Suitable pH active components, such as buffering agents or pH-adjusting agents, that can be used in an ophthalmic formulation according to the invention include, but are not limited to, acids, such as boric acid, citric acid, hydrochloric acid, and salts thereof; and alkali metal salts, such as disodium phosphate, monosodium phosphate, sodium borate, sodium citrate, sodium hydroxide, and potassium phosphates.

According to embodiments of the invention, the pH of an ophthalmic formulation can vary from about 5.0 to 8.0, such as 5.0, 5.5, 6.0, 6.5, 7.0, 7.5, or 8.0. Preferably, the pH is between about 6.0 and 7.5. The pH can be adjusted to control the particle size distribution of the tyrosine kinase inhibitor in the ophthalmic formulation. The pH can also be adjusted to provide for optimal chemical stability of the active ingredient.

According to preferred embodiments of the invention, the tonicity of an ophthalmic formulation is isotonic, or slightly hypotonic as compared to tears, in order to combat any hypertonicity of tears caused by evaporation and/or disease. For example, the osmolality of an isotonic or slightly hypotonic ophthalmic formulation of the invention can be about 250-300 milliosmoles per kilogram (mOsm/kg). A tonicity adjustor can be used to bring the osmolality of the formulation to a level at or near 250-350 mOsm/kg. Suitable tonicity adjustors that can be used include, but are not limited to, ionic and nonionic osmotic adjusting agents such as sodium chloride, potassium chloride, dextran, cyclodextrins, mannitol, dextrose, glycerol, sorbitol, boric acid, borax and propylene glycol and combinations thereof.

Preservatives that can be used in an ophthalmic formulation according to the invention include, but are not limited to, benzalkonium chloride, cetrimide, cetylpyridinium chloride, benzododecinium bromide, benzethonium chloride, thiomersal, chlorobutanol, benzyl alcohol, phenoxyethanol, phenylethyl alcohol, sorbic acid, methyl and propyl parabens, chlorhexidine digluconate, EDTA, polyquad, purite, perborate-based preservatives, other mercuric compounds, zinc polyol complexes, or mixtures thereof.

In a particular embodiment of the invention, benzalkonium chloride is included in the ophthalmic formulation as a preservative. The benzalkonium chloride is preferably present in an amount from about 0.001 to 0.02% w/v, such as 0.001%, 0.005%, 0.01%, or 0.02%, and most preferably about 0.005% w/v.

According to embodiments of the invention, a concentration of the tyrosine kinase inhibitor in an ophthalmic formulation ranges from about 0.01% to about 10% w/v, such as 0.01%, 0.03%, 0.05%, 0.1%, 0.3%, 0.5%, 1%, 2%, 3%, 4%, 5%, 6%, 7%, 8%, 9%, or 10%.

As used herein, a "particle of a tyrosine kinase inhibitor" refers to a particle comprising the tyrosine kinase inhibitor. A "particle" as used herein can be a droplet, vesicle, a lipsome, a micelle, etc. According to embodiments of the invention, a particle of a tyrosine kinase inhibitor can optionally comprise other ingredients, such as phosphocholine, fatty acid glycerides, PLGA and PLA.

In certain embodiments of the invention, an ophthalmic formulation comprises "micronized," preferably "nanonized," particles that comprise a tyrosine kinase inhibitor, such as nanonized or micronized particles of Nintedanib, Sorafenib, Axitinib, or Pazopanib.

As used herein, the terms "nanonized particle," "nano-sized particle," "nanoparticle," and "sub-micron particle" all refer to a particle comprising a therapeutically active compound having an average particle diameter that is in the sub-micron range, and ranges from about 1 nanometer (nm) to less than about 1000 nm, preferably 100 nm to 900 nm, and more preferably about 200 nm to about 800 nm. The term "nanonize" refers to a process of reducing the particle size, i.e., the average diameter of the particle, into the nanometer range.

As used herein, the terms "micronized particle," "micro-sized particle," and "microparticle" all refer to a particle comprising a therapeutically active compound having an average particle diameter that ranges from about 0.5 μm to about 1000 μm, preferably about 0.5 μm to about 100 μm, and more preferably about 0.5 μm to about 10 μm. The term "micronize" refers to a process of reducing the particle size, i.e., the average diameter of the particle, down to a few microns, such as in the range of about 1 μm to about 10 μm.

In one embodiment of the invention, an ophthalmic formulation is a liquid suspension. The liquid suspension is preferably suitable for topical administration. The liquid suspension can be a "nanosuspension" or a "microsuspension."

A "nanosuspension" as used herein refers to a suspension comprising particles of a tyrosine kinase inhibitor with at least a majority of the particles in the suspension as nanoparticles having an average particle diameter of less than about 1 μm. A nanosuspension can also have a few particles in the suspension having an average particle diameter greater than about 1 μm. For a nanosuspension for topical ocular use, the $D_{90}$ particle size is about 1 μm or less than 1.5 μm, and the $D_{50}$ particle size is less than 1 μm. The $D_{90}$ particle size of a liquid suspension is the diameter at which 90% by volume of the particles in the suspension are smaller in their longest dimension, as measured by any conventional particle size measuring technique known to those skilled in the art. The $D_{50}$ particle size of a liquid suspension is the diameter at which 50% by volume of the particles in the suspension are smaller in their longest dimension, as measured by any conventional particle size measuring technique known to those skilled in the art. The $D_{50}$ particle size is therefore a measure of volume median particle size, but is sometimes referred to as "average" or "mean" particle size. Techniques for determining particle size include, but are not limited to, sedimentation field flow fractionation, photon correlation spectroscopy, laser light scattering, and disk centrifugation.

A "microsuspension" as used herein refers to a suspension comprising particles of a tyrosine kinase inhibitor with at least a majority of the particles in the suspension as microparticles having an average particle diameter of about 1 μm to 1000 μm. A microsuspension can also have a few particles in the suspension having an average particle diameter less than about 1 μm. For a microsuspension for topical ocular use, the $D_{90}$ particle size is about less than 20 μm, and the $D_{50}$ particle size is about less than 10 μm.

In one embodiment of the invention, an ophthalmic formulation comprises nanoparticles or microparticles comprising Nintedanib, or a prodrug thereof, or a pharmaceutically acceptable salt thereof, such as Nintedanib ethanesulfonate.

In another embodiment of the invention, an ophthalmic formulation comprises nanoparticles or microparticles comprising Axitinib, or a prodrug thereof, or a pharmaceutically acceptable salt thereof.

In another embodiment of the invention, an ophthalmic formulation comprises nanoparticles or microparticles comprising Sorafenib, or a prodrug thereof, or a pharmaceutically acceptable salt thereof.

In another embodiment of the invention, an ophthalmic formulation comprises nanoparticles or microparticles comprising Pazopanib, or a prodrug thereof, or a pharmaceutically acceptable salt thereof.

In a preferred embodiment, an ophthalmic formulation comprises nanoparticles comprising a tyrosine kinase inhibitor having a $D_{90}$ particle size of less than 1 μm.

Liquid medium can be used in preparing solutions, suspensions and emulsions as ophthalmic formulations of the invention. For example, the tyrosine kinase inhibitor or nanoparticles thereof described herein can be suspended in a pharmaceutically acceptable liquid medium such as water, an organic solvent, a mixture of water and one or more organic solvents, or pharmaceutically acceptable oils or fats. The liquid medium can contain other suitable pharmaceutical additives including, but not limited to, surfactants, preservatives, viscosity regulators, pH-adjusting agents, stabilizers, and osmo-regulators known to those skilled in the art in view of the present disclosure.

Micronized or nanonized particles comprising a tyrosine kinase inhibitor for use in the ophthalmic formulation of the invention can be made using any technique known to those skilled in the art in view of the present disclosure. Examples of techniques for producing micronized or nanonized particles include, but are not limited to, milling, homogenization, precipitation, freezing, template emulsion techniques, liposome formation, emulsion, microemulsion method, solvent extraction/evaporation methods, supercritical fluid technology, spray drying, ultrasonic technology, or any combination thereof. For example, homogenization and milling processes can be combined with a precipitation step in order to achieve smaller particles of narrower size distribution.

In one embodiment, microparticles or nanoparticles comprising a tyrosine kinase inhibitor are made by dry or wet milling. Examples of mills commonly used involve dry-type mills, such as jet mill, conventional and planetary ball mill, vibrational rod mill, and hammer and knife mill. These dry-type mills are used to grind a drug alone to afford particles of several microns in diameter. However, it is difficult to obtain finer particles, particularly submicron particles of less than 1 μm in diameter, using conventional dry milling methods. It has been further noted that a wet milling may be useful to further reduce particle size (see, e.g., (Lachman et al., "The Theory and Practice of Industrial Pharmacy," Milling, 45 (1986)). For wet milling, media mills, such as planetary ball and bead mills which use balls or beads as the grinding media, respectively, and medialess mills, such as a high-pressure homogenizer, are commonly used. A typical wet milling process comprises dispersing a compound in a liquid dispersion medium in which the compound is poorly soluble, followed by applying mechanical means in the presence of grinding media to obtain a dispersion in which the particle size of the compound is reduced to the desired average particle diameter. The dispersion medium can be, for example, water, safflower oil, ethanol, t-butanol, glycerin, polyethylene glycol (PEG), hexane, or glycol. The particle size of the compound can also be reduced by milling in the presence of at least one surface stabilizer. Alternatively, the compound can be contacted with one or more surface stabilizers after attrition. Other components, such as a diluent, can be added to a composition containing the compound and surface stabilizer during the size reduction process. Dispersions can be manufactured continuously or in a batch mode.

The mechanical means applied to reduce the particle size during the milling process can take the form of a dispersion mill. Suitable dispersion mills include a ball mill, an attrition mill, a vibratory mill, and media mills such as a sand mill and a bead mill. Preferably, a media mill is used due to the relatively shorter milling time required to provide the desired reduction in particle size. For media milling, the apparent viscosity of a mixture prior to milling (e.g., mixture containing the active pharmaceutical ingredient and wetting agent dissolved in water) is preferably between 100 to about 1000 centipoise. For ball milling, the apparent viscosity of a mixture prior to milling (e.g., mixture containing the active pharmaceutical ingredient and wetting agent dissolved in water) is preferably between 1 to about 100 centipoise. Such ranges tend to afford an optimal balance between efficient particle size reduction and media erosion, but are in no way limiting. Any other mechanical means known to those skilled in the art in view of the present disclosure can be used to reduce the particle size.

Any material known to those skilled in the art in view of the present disclosure can be used as the grinding media for particle size reduction during milling. For example, the grinding media is selected from rigid media, preferably spherical or particulate in form, and ranging in size from about 0.01 mm to 3 mm, and more preferably 0.01 mm to less than 1 mm. For fine grinding, the grinding media is preferably from 0.02 to 2 mm, and more preferably from 0.03 to 1 mm in size. Such grinding media can provide particles for use in the invention with shorter processing times and impart less wear to the milling equipment, which are desirable advantages. Non-limiting examples of grinding material include zirconium oxide, such as 95% ZrO stabilized with magnesium; zirconium silicate; ceramic; stainless steel; titanium; aluminum; yttrium; and glass. The grinding media can contain particles that are preferably spherical in shape, e.g., beads, made of polymeric resin, glass, zirconium silicate, or other suitable material. Alternatively, the grinding media can comprise a core having a coating of a polymeric resin adhered thereon.

After the particle reduction step by grinding during the milling process, the grinding media can be separated from milled nanoparticles using conventional separation techniques in a secondary process such as by simple filtration, sieving through a mesh filter or screen, and the like. Other separation techniques, such as centrifugation can also be employed. Alternatively, a screen can be utilized during the milling process to remove the grinding media following completion of particle size reduction.

According to embodiments of the invention, precipitation can be used to form nanoparticles of a tyrosine kinase inhibitor suitable for use in the ophthalmic formulations of the invention. Precipitation includes nanoprecipitation. In general, nanoprecipitation is the nucleation of small aggregates of macromolecules followed by aggregation of these nuclei. One nanoprecipitation process that can be used is nanomorph, which is a process by which molecules with low aqueous solubility are converted from a crystalline state into amorphous nanoparticles at the industrial scale by dissolving the tyrosine kinase inhibitor in a solvent, and feeding into a mixing chamber to rapidly mix with a non-solvent for the active pharmaceutical ingredient (API) (i.e., solvent in which the API is not very soluble, or does not dissolve well in). Another nanoprecipitation approach involves the use of the MicroJet Reactor technology, by which organic solutions of the tyrosine kinase inhibitor and one or more polymers, such as HPMC, sodium carboxymethylcellulose, carbomer, polycarbophil, PEG, and HA collide with a non-solvent for the API in the middle of a gas-filled chamber. The small diameter combined with a high velocity of the jets result in a very fast and intensive mixing and precipitation of insoluble reaction products. The influx of gas carries the dispersion out of the reaction chamber. Although particle size and size distribution depend on desolvation velocity and precipitation kinetics of polymer(s) and compound, small particles with narrow size distribution can be achieved by this method.

Another method of forming nanoparticles that can be used in accordance with the invention is template emulsion. Template emulsion creates nanostructured particles with controlled particle size distribution and rapid dissolution performance. Template emulsion involves preparing an oil-in-water emulsion, then swelling in a non-aqueous solution comprising the selected tyrosine kinase inhibitor and stabilizer. The solvent and water are then removed. The resulting particle size distribution of the tyrosine kinase inhibitor is usually based on the size of the emulsion droplets prior to loading with the tyrosine kinase inhibitor, and optimizing the size of the emulsion droplets can be used to control the particle size distribution of the tyrosine kinase inhibitor. Furthermore, through selected use of solvents and stabilizers, emulsion stability is achieved with no or suppressed Oswald ripening. By controlling the processing conditions, such as the size of emulsion droplets, solvents, and stabilizers, various particle morphologies can be achieved.

An exemplary homogenization method, i.e., forming a suspension comprising nanoparticles or microparticles, and more preferably a suspension comprising nanoparticles, comprises dispersing particles of a tyrosine kinase inhibitor, a prodrug thereof, or a pharmaceutically acceptable salt thereof, in a liquid dispersion medium, followed by homogenization to reduce the particle size to the desired effective average particle size. Specifically, in a high pressure homogenization process, a pre-suspension of the particles of tyrosine kinase inhibitor having a particle size in the micrometer range passes through a very small homogenizer gap. This creates cavitation forces of high turbulence and shear, combined with compression, acceleration, pressure drop, and impact, which are sufficiently high to disintegrate micropar-ticles of the tyrosine kinase inhibitor to nanoparticles as the suspension leaves the gap and normal air pressure is reached again (Microfluidizer® processor, Microfluidics, USA). The homogenization pressure and number of homogenization cycles are important parameters in optimizing the process, and one of ordinary skill in the art would be able to determine the optimum values for such parameters in order to achieve the desired results.

In other embodiments of the invention, an ophthalmic formulation comprises particles of a tyrosine kinase inhibitor, or a prodrug thereof, or pharmaceutically acceptable salt thereof dispersed in a composition containing a bioadhesive material. A bioadhesive material can be a cationic bioadhesive or an anionic bioadhesive. Particles of the tyrosine kinase inhibitor, such as microparticles or nanoparticles, and preferably nanoparticles of the tyrosine kinase inhibitor, can be contacted with a solution comprising a bioadhesive that associates with and/or coats the particles. In some embodiments, particles having one or more coatings of the bioadhesive can be formed by layer-by-layer methods. In other embodiments, a hollow matrix can first be assembled from the bioadhesive in the solution before the tyrosine kinase inhibitor is encapsulated to form the particle. The bioadhesive coating can be further stabilized by the addition of an oppositely charged polymer, which forms a firm electrostatic complex with the bioadhesive coating. This results in the appearance of a very thin, but stable layer or shell around each nanoparticle. This shell can prevent particle agglomeration, and can be easily and reproducibly formed on the surface of the nanoparticle.

A particle coated with the bioadhesive as described herein can have any suitable shape and/or size. In some embodiments, a coated particle has a shape substantially similar to the shape of the core. According to embodiments of the invention, the coated particle described herein can be a nanoparticle or a microparticle.

In certain embodiments, the particles of the tyrosine kinase inhibitor described herein, such as nanoparticles or microparticles, can further comprise surface-altering moieties and/or agents that affect the zeta-potential of the particle. Examples of such surface-altering moieties and/or agents that can be employed in the invention include, but are not limited to, Hyaluronic acid, Carbomer, Polycarbophil, CMC-Na, Benzalkonium chloride, Cetalkonium chloride, Benzethonium chloride, Chitosan, Oleylamine, and Cetrimide. The zeta potential of a coated particle can be, for example, at least about −100 mV, at least about −75 mV, at least about −50 mV, at least about −30 mV, at least about −20 mV, at least about −10 mV, at least about −5 mV, at least about 5 mV, at least about 10 mV, at least about 20 mV, at least about 30 mV, at least about 50 mV, at least about 75 mV, or at least about 100 mV. Preferably, the coated particle has a zeta potential in a range of about −30 mV to 30 mV, which is an optimal range of zeta potential for maintaining suspension stability. However, other ranges are also possible.

According to embodiments of the invention, a bioadhesive offers advantages such as localizing a dosage form within a particular region, increasing drug bioavailability, promoting contact with a surface for a longer time, and reducing dosage frequency. In certain instances, the bioadhesive can be biodegradable and/or biocompatible polymers which include, but are not limited to, hyaluronic acid (HA), derivatives of HA and salts of HA, such as cross-linked hyaluronic acid, sodium hyaluronate, and cationic derivative of HA; gelatin, chondroitin sulfate, collagen, cross-linked collagen, collagen derivatives (such as succinylated collagen or methylated collagen), chitosan, chitosan derivatives (such as methylpyrrolidone-chitosan), chitin and other glycosaminoglycans, stearylamine, oleylamine, polyethylenimine (PEI), poly-L-lysine (PLL), cationic lipids such as N-(1-(2,3-dioleoyloxy)propyl)-N,N,N trimethylammonium (DOTAP) chloride and dioleoyl phosphatidylethanolamine (DOPE), and quaternary ammonium compounds and their derivatives, or any suitable combination thereof.

The invention also relates to use of the ophthalmic formulations described herein to treat or prevent ocular disorders, and particularly ocular surface diseases. According to embodiments of the invention, a method of treating an ocular surface disease in a subject in need thereof comprises administering to an eye of the subject an ophthalmic formulation of the invention. Any of the ophthalmic formulations described herein can be used in a method of the invention. Preferably, an ophthalmic formulation of the invention is topically administered to the eye of the subject. It is believed that ophthalmic formulations of the invention have advantageous properties in terms of drug release, bioavailability, and/or compliance in mammals that make them suitable for use in treating ocular disorders, such as ocular surface diseases.

As used herein, "subject" means any animal, preferably a mammal, most preferably a human, to whom will be or has been treated by a method according to an embodiment of the invention. The term "mammal" as used herein, encompasses any mammal. Examples of mammals include, but are not limited to, cows, horses, sheep, pigs, cats, dogs, mice, rats, rabbits, guinea pigs, non-human primates (NHPs) such as monkeys or apes, humans, etc., and more preferably a human.

An "ocular surface disease" as used herein refers to any disorder of the surface of the eye, which is the exposed layer that forms the front of the eye. Examples of ocular surface diseases that can be treated according to a method of the invention include, but are not limited to, angiogenesis in the front of the eye, such as corneal angiogenesis following e.g. keratitis, corneal transplantation, or keratoplasty; conjunctival degeneration (pinguecula) with slow proliferation; conjunctival papilloma, corneal angiogenesis due to hypoxia; hyperemia; hyperemia associated with pterygium; hyperthyroidism-induced eye congestion; immune or surgery related dry eyes; neovascular glaucoma (NVG); ocular cancer, pterygium conjunctivae; recurrent pterygium; Steven Johnson syndrome; and stye.

In preferred embodiments of the invention, the ocular surface disease to be treated is hyperemia associated with pterygium, pterygium conjunctivae, recurrent pterygium, or corneal angiogenesis.

Ptergyium is a condition of the eye characterized by a vascular, pink, fleshy growth on the white of the eye originating from the conjunctiva, which can spread into the corneal limbus. The lesion can take any shape, but is typically triangular or wing-shaped. A pterygium lesion usually has three parts: a cap, a head, and a body/tail. The cap is a flat zone on the cornea containing mostly fibroblasts; the head is a vascular area behind the cap that is firmly attached to the cornea; and the body/tail is the mobile area over the bulbar conjunctiva. Patients are typically asymptomatic until the lesion spreads into the cornea, where it can cause blurred vision. However, some patients do experience symptoms, such as burning, a gritty feeling in the eye, or a foreign body sensation early in the disease progression. Pterygium lesions can be primary lesions, or recurrent lesions. Recurrent lesions are lesions that return after removal of the initial primary lesion, such as by surgical removal. Recurrent pterygium refers to pterygium lesions that occur after an initial or primary lesion has already been removed or treated. Pterygium can also be associated with other conditions and side effects, such as hyperemia. Hyperemia (redness) generally refers to an increase in blood flow to the eye resulting in increased redness of the eye. Hyperemia can occur on its own (primary), or it can be a symptom associated with one or more other ocular diseases (secondary), such as pterygium.

In accordance with other embodiments of the invention, the ophthalmic formulations comprising Nintedanib in a therapeutically effective amount may also be administered for example, via intravitreal injection to the back/posterior of the eye, for the treatment of other ocular diseases characterized by neovascularization, vascular permeability, edema, or inflammation. These ocular diseases include but are not limited to ocular inflammation and/or ocular angiogenesis such as aged-related macular degeneration (AMD), proliferative and non-proliferative diabetic retinopathy, choroidal neovascularization, uveitis, rubeosis iridis, and neovascular glaucoma.

The terms "treat," "treating," and "treatment" as used herein refer to administering a composition to a subject to achieve a desired therapeutic or clinical outcome in the subject. In one embodiment, the terms "treat," "treating," and "treatment" refer to administering an ophthalmic formulation of the invention to reduce, alleviate or slow the progression or development of an ocular surface disease. In yet another embodiment, the terms "treat," "treating," and "treatment" refer to administering an ophthalmic formulation of the invention to inhibit or reduce corneal neovascularization and/or cell proliferation in the eye. In yet another embodiment, the terms "treat," "treating," and "treatment" refer to administering an ophthalmic formulation of the invention to slow the progression or development of new blood vessels in the cornea (i.e., corneal neovascularization).

In particular embodiments of the invention, when used with reference to pterygium, the terms "treat," "treating," and "treatment" refer to preventing the growth of recurrent lesions or reducing the recurrence rate of such lesions; slowing, delaying, or preventing the spread of lesions from the conjunctiva into the corneal region; reducing or alleviating one or more symptoms associated with pterygium, such as a burning sensation or gritty feeling in the eye; regression of lesion from the corneal region; and/or reducing, slowing the progression of, or alleviating secondary conditions associated with pterygium, such as hyperemia.

According to embodiments of the invention, an ophthalmic formulation can be administered by any method known to those skilled in the art in view of the present disclosure, such as by topical administration, subconjunctival injection, or ophthalmic delivery by a device such as contact lens. In a preferred embodiment, the ophthalmic formulation is topically administered, e.g., by eye drops or by swabbing, insertion of a contact lens loaded with the drug, or an erodible or non-erodible insert placed in the cul-de-sac of the eye. For example, a liquid nanosuspension can be administered as eye drops. Nanoparticles in the form of eye drops can quickly access and associate with the cornea and conjunctiva, and those nanoparticles residing on the cornea and conjunctiva can contribute to drug levels predominantly in the ocular tissues of the anterior segment of the eye. An ophthalmic formulation can be administered to any part of the eye, and is preferably administered to the surface of the eye for the treatment of an ocular surface disease.

Parameters such as the dosage amount, frequency of administration, and duration of administration of an ophthalmic formulation to a subject according to an embodiment of the invention are not limited in any particular way. The optimum values of such parameters can depend on a variety of factors, such as the subject to be treated, the particular ocular surface disease to be treated, the severity of the disease, etc., and one of ordinary skill in the art will be able to determine the optimum values for such parameters in order to achieve the desired therapeutic or clinical outcome. For example, an ophthalmic formulation can be administered once per day, or more than once per day, such as twice, three times, four times, etc. An exemplary and non-limiting dosing regimen comprises administering an ophthalmic formulation as eye drops three times per day for a duration of one to two weeks.

The invention also relates to a method of preparing an ophthalmic formulation, including a method of preparing any of the ophthalmic formulations described herein. According to embodiments of the invention, a method of preparing an ophthalmic formulation comprises optionally forming nanoparticles or microparticles of a tyrosine kinase inhibitor selected from the group consisting of Axitinib, Nintedanib, Sorafenib, Pazopanib, prodrugs thereof, and pharmaceutically acceptable salts thereof, and combining the tyrosine kinase inhibitor, or microparticles or nanoparticles thereof with at least one pharmaceutically acceptable excipient.

According to embodiments of the invention, the nanoparticles or microparticles can be formed in the presence of surfactant. Any of the surfactants described herein can be used including, but not limited to, Tween 80, Tween 20, poloxamer 188, poloxamer 407, or tyloxapol, and preferably tyloxapol. Any of the methods described herein can be used to form the nanoparticles or microparticles. Preferably, milling is used, such as a ball-milling process.

The following examples of the invention are to further illustrate the nature of the invention. It should be understood that the following examples do not limit the invention and that the scope of the invention is to be determined by the appended claims.

EMBODIMENTS

Embodiment 1 is an ophthalmic formulation comprising a therapeutically effective amount of Nintedanib, a prodrug thereof, or a pharmaceutically acceptable salt thereof, and at least one pharmaceutically acceptable excipient.

Embodiment 2 is the ophthalmic formulation of embodiment 1, wherein the at least one pharmaceutically acceptable excipient is selected from the group consisting of surfactants, preservatives, viscosity regulators, pH-adjusting agents, stabilizers, and osmo-regulators.

Embodiment 3 is the ophthalmic formulation of embodiment 2, wherein the surfactant is selected from the group consisting of Tween 80, Tween 20, Poloxamer 188, poloxamer 407 and Tyloxapol.

Embodiment 4 is the ophthalmic formulation of embodiment 3, wherein the surfactant is Tyloxapol.

Embodiment 5 is the ophthalmic formulation of embodiment 2, wherein the viscosity regulator is selected from the group consisting of HPMC, Sodium Carboxymethylcellulose, Carbomer, Polycarbophil, PEG and HA or its salts and derivatives.

Embodiment 6 is the ophthalmic formulation according to any one of embodiments 1 to 5, wherein the ophthalmic formulation comprises micronized particles or nanonized particles of Nintedanib, the prodrug thereof, or the pharmaceutically acceptable salt thereof.

Embodiment 7 is the ophthalmic formulation according to any one of embodiments 1 to 6, wherein the formulation is a liquid suspension, preferably a nanosuspension, for topical ocular administration.

Embodiment 8 is the ophthalmic formulation according to any one of embodiments 1 to 7, wherein a concentration of Nintedanib, the prodrug thereof, or pharmaceutically acceptable salt thereof is 0.01% to 10% w/v.

Embodiment 9 is an ophthalmic formulation comprising a therapeutically effective amount of micronized or nanonized particles comprising a tyrosine kinase inhibitor selected from the group consisting of Axitinib, Nintedanib, Sorafenib, Pazopanib, a prodrug thereof, and a pharmaceutically acceptable salt thereof, and at least one pharmaceutically acceptable excipient.

Embodiment 10 is the ophthalmic formulation of embodiment 9, wherein a concentration of the tyrosine kinase inhibitor is 0.01% to 10% w/v.

Embodiment 11 is the ophthalmic formulation according to embodiment 9 or embodiment 10, wherein the formulation is a liquid suspension, preferably a nanosuspension, for topical ocular administration.

Embodiment 12 is a method of treating an ocular surface disease in a subject in need thereof, the method comprising administering to an eye of the subject the ophthalmic formulation according to any one of embodiments 1 to 11.

Embodiment 13 is the method of embodiment 12, wherein the ocular surface disease is selected from the group consisting of angiogenesis in the front of the eye; corneal angiogenesis following keratitis, corneal transplantation, or keratoplasty; conjunctival degeneration (pinguecula) with slow proliferation; conjunctival papilloma; corneal angiogenesis due to hypoxia; hyperemia; hyperemia associated with pterygium; hyperthyroidism-induced eye congestion; dry eyes (including but not limited to immune-related, inflammation-related or surgery-related); neovascular glaucoma (NVG); ocular cancer; pterygium conjunctivae; recurrent pterygium; Steven Johnson syndrome; and stye.

Embodiment 14 is the method of embodiment 13, wherein the ocular surface disease is hyperemia associated with pterygium, pterygium conjunctivae, or recurrent pterygium.

Embodiment 15 is a method of preparing the ophthalmic formulation of any one of embodiments 1 to 11, comprising optionally forming microparticles or nanoparticles comprising a tyrosine kinase inhibitor selected from the group consisting of Axitinib, Nintedanib, Sorafenib, Pazopanib, a prodrug thereof, and a pharmaceutically acceptable salt thereof, and mixing the tyrosine kinase inhibitor or the nanoparticles or microparticles thereof with at least one pharmaceutically acceptable excipient.

Embodiment 16 is the method of embodiment 15, wherein the microparticles or nanoparticles are formed by a milling process.

Embodiment 17 is the method of embodiment 15 or embodiment 16, wherein the microparticles or nanoparticles are formed in the presence of tyloxapol.

Embodiment 18 is the ophthalmic formulation of any one of embodiments 9 to 11, wherein the nanoparticles have a D90 particle size of less than 1 μm.

Embodiment 19 is use of the ophthalmic formulation of any one of embodiments 1 to 11 in the preparation of a medicament for treating an ocular surface disease.

Embodiment 20 is the ophthalmic formulation of any one of embodiments 1 to 11 for use in treating an ocular surface disease.

Embodiment 21 is Nintedanib, a prodrug thereof, or a pharmaceutically acceptable salt thereof for use in treating an ocular surface disease.

Embodiment 22 is use of Nintedanib, prodrug thereof, or a pharmaceutically acceptable salt thereof in the preparation of a medicament for treating an ocular surface disease.

Embodiment 23 is an ophthalmic formulation comprising:
(a) a therapeutically effective amount of nanoparticles comprising Nintedanib or a pharmaceutically acceptable salt thereof in a concentration of about 0.1% w/v to about 10% w/v;
(b) about 0.01% to 0.3% tyloxapol; and
(c) about 0.1% to 1% HPMC.
wherein the formulation is a liquid suspension for topical administration.

Embodiment 24 is the ophthalmic formulation of embodiment 23 having a $D_{10}$ particle size in a range of about 0.1-0.5 µm.

Embodiment 25 is the ophthalmic formulation of embodiment 23 or embodiment 24 having a $D_{50}$ particle size in a range of about 0.4-1.5 µm.

Embodiment 26 is the ophthalmic formulation of any one of embodiments 23 to 25 having a $D_{90}$ particle size in a range of about 0.5-3.0 µm.

Embodiment 27 is a method of treating an ocular surface disease in a subject in need thereof, the method comprising administering to an eye of the subject the ophthalmic formulation according to any one of embodiments 23 to 26.

Embodiment 28 is the method of embodiment 27, wherein the ocular surface disease is selected from the group consisting of angiogenesis in the front of the eye; corneal angiogenesis following keratitis, corneal transplantation, or keratoplasty; conjunctival degeneration (pinguecula) with slow proliferation; conjunctival papilloma; corneal angiogenesis due to hypoxia; hyperemia; hyperemia associated with pterygium; hyperthyroidism-induced eye congestion; dry eyes (including but not limited to immune-related, inflammation-related or surgery-related); neovascular glaucoma (NVG); ocular cancer; pterygium conjunctivae; recurrent pterygium; Steven Johnson syndrome; and stye.

Embodiment 29 is the method of embodiment 28, wherein the ocular surface disease is hyperemia associated with pterygium, pterygium conjunctivae, recurrent pterygium, or corneal angiogenesis.

EXAMPLES

Example 1: Preparation of Ophthalmic Suspension Containing Nintedanib Ethanesulfonate A 0.3% Nintedanib Ethanesulfonate ophthalmic suspension having the components listed in Table 1 below was prepared.

TABLE 1

| Ingredient | w/v (%) |
| --- | --- |
| Nintedanib Ethanesulfonate | 0.3 |
| HPMC (Methocel F4M) | 1.0 |
| Polysorbate 80 | 0.1 |
| Sodium Phosphate Dibasic Heptahydrate | 0.27 |
| Sodium Phosphate Monobasic Monohydrate | 0.03 |
| Sodium Chloride | 0.85 |
| Benzalkonium Chloride (BAK) | 0.005 |
| Edetate Disodium | 0.1 |
| 1N Sodium Hydroxide | pH 7.4 |
| Purified Water | QS |

Vehicle Preparation

First, 2% hydroxypropyl methylcellulose (HPMC) stock and 5× buffer preparation were mixed, followed by addition of a sufficient quantity (QS) of purified water to obtain a vehicle having a final concentration of 1% HPMC stock and 20% buffer for formulating the ophthalmic liquid suspension. The HPMC stock and buffer preparation were prepared as follows.

HPMC Stock (2%)

For the preparation of 200 mL HPMC, the following procedure was followed:
(1) Water (150 mL) was heated to about 80° C. (under continuous stirring);
(2) HPMC (4 g) was gradually added to the water (under constant stirring) to form an HPMC solution;
(3) The HPMC solution was mixed until it was well dispersed and suspended;
(4) The HPMC solution was quantitatively transferred to a 200 mL volumetric flask and purified water was added to near final volume;
(5) The volumetric flask was placed in a water bath under constant stirring to cool to room temperature; and
(6) Purified water was added to a final volume of 200 mL, and mixed well.

Buffer Preparation (5×)

For the preparation of 200 mL of 5× buffer, the following procedure was followed:
(1) Sodium Phosphate Dibasic Heptahydrate (2.7 mg), Sodium Phosphate Monobasic Monohydrate (0.3 g), Sodium Chloride (8.5 g), Edetate Disodium (1.0 g), Polysorbate 80 (1.0 g), and Benzalkonium Chloride (0.050 g) were dissolved in 180 mL of purified water;
(2) The pH was adjusted to 7.4 with 1 N NaOH;
(3) The buffer was transferred to a 200 mL volumetric flask; and
(4) Purified water was added to a final volume of 200 mL, and the buffer was mixed well.

Preparation of Liquid Suspension

Next, the liquid suspension of Nintedanib Ethanesulfonate (0.3% w/w) was prepared in accordance with the following procedure:
(1) Nintedanib Ethanesulfonate (45.37 mg) and vehicle (14.97515 g) were weighed into a 20 mL scintillation vial, a stir bar was added, and the vial was securely capped;
(2) The vial was swirled with sonication for about 1 minute;
(3) The vial was shaken for about 30 seconds to disperse large API aggregates;
(4) The vial was swirled with sonication for about 1 minute;
(5) The vial was mixed on magnetic stir plate at high speed for 5 minutes;
(6) Steps (3)-(5) were repeated as needed, until Nintedanib Ethanesulfonate was uniformly dispersed/suspended and no visible aggregate remained (estimated total mixing and sonication time was about 1.25 hours);
(7) The vial was mixed on the magnetic stirrer for an additional 10 minutes to obtain an ophthalmic liquid suspension containing 0.3% Nintedanib Ethanesulfonate.

Suspension Uniformity Testing

Suspension uniformity for the 0.3% Nintedanib Ethanesulfonate liquid suspension was determined by using a high performance liquid chromatography (HPLC) method in accordance with the following setup and preparations.

Instrument Setup:

The HPLC method was performed using an instrument with the parameters set as shown in Table 2.

TABLE 2

| | |
|---|---|
| Instrument: | HPLC equipped with a UV detector |
| Column: | Sunfire C18, 5 μm particles, 4.6 mm × 250 mm |
| Detector: | UV Wavelength at 255 nm |
| Column Temperature: | Ambient |
| Autosampler Temperature: | Ambient |
| Injection Volume: | 10 μL |
| Pump Flow Rate: | 1.0 mL/minute |
| Mobile Phase A: | 0.05% Trifluoroacetic Acid |
| Mobile Phase B: | 0.05% Trifluoroacetic Acid in, Water:Acetonitrile (10:90 v/v) |
| Run Time: | 15 Minutes |

Diluent Preparation:

Water and methanol were mixed in a 1:1 ratio by volume to prepare the diluent. For the preparation of 1 L of diluent, 500 mL water was mixed with 500 mL of methanol.

Vehicle Preparation:

Vehicle (0.5 g) was diluted in 25 mL diluent and mixed well.

Nintedanib Ethanesulfonate Standard Preparation:

Nintedanib Ethanesulfonate (50.33 mg) was weighed into a 50 mL volumetric flask, diluent was added (40 mL), and the mixture was sonicated to dissolve. The mixture was diluted with diluent to obtain a standard stock solution of 1.0066 mg/mL of Nintedanib Ethanesulfonate. The standard stock solution was further diluted with diluent and mixed well to obtain a standard preparation of 0.0604 mg/mL of Nintedanib Ethanesulfonate.

Sample Preparation:

The 0.3% Nintedanib Ethanesulfonate liquid suspension (0.5 g) was weighed into a 25 mL volumetric flask, diluted with diluent (20 mL), and mixed and sonicated to dissolve. The mixture was further diluted with diluent and mixed well to obtain a sample preparation containing 0.060 mg/mL of Nintedanib Ethanesulfonate.

Samples from top, middle, and bottom locations of the scintillation vial were taken immediately after the suspension was prepared, after 8 hours at room temperature (bench top under constant mix), and after sitting at room temperature for 1 hour with no mixing. The samples were analyzed by HPLC. A total of nine samples were tested.

The results of suspension uniformity testing assay for the 0.3% Nintedanib Ethanesulfonate suspension showed good suspension uniformity at all time points and for all locations in the vial, with an overall % relative standard deviation (% RSD) of the nine samples tested of less than 2%.

Particle Size Distribution Analysis

Particle size analysis of the 0.3% Nintedanib Ethanesulfonate ophthalmic liquid suspension was performed in triplicate using a Laser Scattering Particle Size Distribution Analyzer LA-950. A summary of the results is shown in Table 3.

TABLE 3

| | Particle Size Distribution (μm) | | |
|---|---|---|---|
| | D10 | D50 | D90 |
| Average (n = 3) | 4.4855 | 7.6814 | 13.3170 |

The results of the particle size distribution analysis testing show that the average particle diameter of the 0.3% Nintedanib Ethanesulfonate suspension prepared as described above is in the micrometer range.

Osmolality and pH

The osmolality of the 0.3% Nintedanib Ethanesulfonate suspension was tested in triplicate and found to be 325 mOsm/kg (n=3). The pH was measured to be 7.18.

Example 2: Preparation of Ophthalmic Suspension Containing Axitinib

A 1% (w/w) Axitinib ophthalmic formulation was prepared as a liquid suspension. The components of the Axitinib liquid suspension are the same as shown in Table 1, except the suspension contained 1% Axitinib rather than 0.3% Nintedanib Ethanesulfonate. The vehicle was also prepared as described above in Example 1.

The Axitinib ophthalmic suspension was prepared according to the following procedure:

(1) Axitinib (150.24 mg) and vehicle (14.8225 g) were weighed into a 20 mL scintillation vial, a stir bar was added, and the vial was securely capped;
(2) The vial was swirled with sonication for about 2 minutes;
(3) The vial was shaken to disperse large aggregates of Axitinib for about 30 seconds;
(4) The vial was sonicated and swirled intermittently for 1 minute;
(5) The vial was mixed on a magnetic stir plate at high speed for 5 minutes:
(6) Steps (3)-(5) were repeated as needed, until Axitinib was uniformly dispersed/suspended and no visible aggregate remained (estimated total mixing and sonication time is about 0.5 hours).
(7) The vial was mixed on the magnetic stirrer for an additional 10 minutes to obtain an ophthalmic liquid suspension containing 1% Axitinib.

Suspension Uniformity Testing

The suspension uniformity for 1% Axitinib was determined using a high performance liquid chromatography (HPLC) method in accordance with the following setup and preparations.

Instrument Setup:

The HPLC method was performed using an instrument with the parameters set as shown in Table 4.

TABLE 4

| | |
|---|---|
| Instrument: | HPLC equipped with a UV detector |
| Column: | Sunfire C18, 5 μm particles, 4.6 mm × 250 mm |
| Detector: | UV Wavelength at 250 nm |
| Column Temperature: | Ambient |
| Autosampler Temperature: | Ambient |
| Injection Volume: | 5 μL |
| Pump Flow Rate: | 1.0 mL/minute |
| Mobile Phase A: | 0.05% Trifluoroacetic Acid in Water |
| Mobile Phase B: | 0.05% Trifluoroacetic Acid in Water:Acetonitrile (10:90, v/v) |
| Run Time: | 17 minutes |

Diluent Preparation:

For the preparation of 1 L of diluent, 650 mL of 0.1% $H_3PO_4$ (~85%) was mixed with 350 mL of water.

Vehicle Preparation:

Vehicle (0.5 g, prepared as described in Example 1) was diluted in 25 mL of diluent and mixed well.

Standard Preparation of Axitinib:

Axitinib (51.12 mg) was mixed with diluent (40 mL) and sonicated to dissolve. The mixture was further diluted with diluent to obtain a standard preparation having a final concentration of 0.2045 mg/mL of Axitinib.

Sample Preparation:

The 1% Axitinib suspension preparation (0.5 g) was weighed out, mixed with diluent (20 mL), and sonicated to dissolve. The mixture was further diluted with diluent and mixed well to obtain sample preparations having a final concentration of about 0.2 mg/mL of Axitinib.

Samples from top, middle, and bottom locations of the scintillation vial were taken immediately after the suspension was prepared, after 8 hours at room temperature (bench top under constant mix), and after sitting at room temperature for 1 hour with no mixing. The samples were analyzed by HPLC. A total of nine samples were tested.

The results of suspension uniformity testing assay for the 1% Axitinib suspension showed good suspension uniformity at all time points and for all locations in the vial, with an overall % relative standard deviation (% RSD) of the nine samples tested of less than 2%.

Particle Size Distribution Analysis

Particle size analysis of the 1% Axitinib ophthalmic liquid suspension was performed in triplicate using a Laser Scattering Particle Size Distribution Analyzer LA-950. A summary of the results is shown in Table 5.

TABLE 5

| | Particle Size Distribution (μm) | | |
|---|---|---|---|
| | D10 | D50 | D90 |
| Average (n = 3) | 1.6361 | 3.9626 | 8.0089 |

The results of the particle size distribution analysis testing show that the average particle diameter of the 1% Axitinib suspension prepared as described above is in the micrometer range. In particular, the ophthalmic suspension has a $D_{10}$ particle size of about 1.6 μm, a $D_{50}$ of about 4.0 μm and a $D_{90}$ of about 8.0 μm.

Osmolality and pH

The osmolality of the 1% Axitinib suspension was tested in triplicate and found to be 307 mOsm/kg (n=3). The pH was measured to be 7.83.

Example 3: Ocular Tolerability Study of the Ophthalmic Suspension

The ocular tolerability was evaluated, and ocular exposure was characterized after a single bilateral (both eyes) topical administration to male Dutch Belted rabbits (3 to 4 months old) having no visible signs of ocular defects. All animals received a topical administration in both eyes of either 0.3% Nintedanib Ethanesulfonate microsuspension, 0.3% Sorafenib Tosylate microsuspension, or 0.3% Axitinib microsuspension. The ophthalmic suspension containing Sorafenib Tosylate was prepared in the same manner as the Nintedanib Ethanesulfonate microsuspension and Axitinib microsuspension as described in Examples 1 and 2, respectively. All groups were dosed three times daily (TID) on Day 1, 2, 3, and once on Day 4. A calibrated positive displacement pipette was used to administer a dose volume of 35 μL/eye onto the globe of each eye.

Clinical observations were conducted at receipt, prior to dosing, and prior to euthanasia. Tolerability assessments were conducted following each dose. Ocular irritation measurements, using the Draize scoring system, were conducted on Day 0 (predose), following the first dose of the day on Days 1 and 3, and immediately prior to the terminal time point on Day 4.

Draize scoring was 0 for all observations during the course of the study, which was in agreement with the daily observations. None of the formulations tested resulted in any extended ocular irritation.

At approximately 2 hours post the final dose on Day 4, rabbits were euthanized via barbiturate overdose prior to both eyes being harvested and dissected for collection of aqueous humor, conjunctiva, and cornea. Following collection, tissues were weighed and snap-frozen on dry ice, and placed in a freezer at −80° C. until processed for analysis. Concentrations of Nintedanib Ethanesulfonate, Sorafenib Tosylate, and Axitinib were quantitated using a qualified LC-MS/MS method in the conjunctiva, cornea, and aqueous humor collected following the terminal time point. The results are shown below in Table 6.

TABLE 6

Mean concentrations of Nintedanib Ethanesulfonate, Sorafenib Tosylate, and Axitinib measured in the conjunctiva, cornea, and aqueous humor.

| Formulation | No. of Eyes | Average Concentration in Conjunctiva (ng/g)[1] | Average Concentration in Cornea (ng/g)[2] | Average Concentration in Aqueous Humor (ng/mL) |
|---|---|---|---|---|
| 0.3% Axitinib liquid suspension | 4 | 783 ± 348 | 666 ± 52.6 | 15.4 ± 3.54 |
| 0.3% Nintedanib Ethanesulfonate liquid suspension | 4 | 5260 ± 1030 | 3910 ± 722 | 4.57 ± 0.904 |
| 0.3% Sorafenib Tosylate liquid suspension | 4 | 762 ± 447 | 857 ± 75.8 | 1.58 ± 0.293 |

[1]ng/g = nanograms of Axitinib, Nintedanib Ethanesulfonate, or Sorafenib Tosylate per gram of conjunctival tissue
[2]ng/g = nanograms of Axitinib, Nintedanib Ethanesulfonate, or Sorafenib Tosylate per gram of corneal tissue In the conjunctiva and cornea, the highest concentrations observed were quantitated as 5260 ng/g and 3910 ng/g respectively, following the administration of ophthalmic suspension containing 0.3% (w/w) Nintedanib Ethanesulfonate. In aqueous humor, the highest concentration of 15.4 ng/mL was quantitated following the dose of 0.3% (w/w) Axitinib.

In summary, all test compounds were well tolerated following topical ocular TID dosing for 3 days. With respect to tissue concentrations, topical ocular dosing with 0.3% (w/w) Nintedanib Ethanesulfonate resulted in the highest conjunctiva and cornea concentration, and 0.3% Axitinib (w/w) the highest aqueous humor concentration.

Example 4: Topical Efficacy of an Ophthalmic Suspension in an Animal Model of Cornea Suture-Induced Neovascularization The aim of this study is to determine whether topical administration (eye drops) of ophthalmic suspensions of the invention result in decreased neovascularization in a rabbit model of cornea suture-induced neovascularization (Campos-Mollo et al., "New Corneal Neovascularization Model in Rabbits for Angiogenesis Research" Ophthalmic Res. (2010) 45, 135-141).

For this study, New Zealand white rabbits at approximately 5 months old with no visible signs of ocular defects were selected. Suture placement was performed on Day 1. Prior to surgery, the right eye of each animal was dilated using a mydriatic agent (1% tropicamide), and the conjunctiva was flushed with approximately 10 mL benzalkonium chloride (Zephiran™) diluted in sterile water, U.S.P. to 1:10,000 (v/v). Saline (0.9%) was also used to flush the eye along with benzalkonium chloride. Animals were anesthetized with isoflurane/oxygen during the procedure. Hydration of the eyes was maintained by irrigation with saline solution, as needed. The procedure was conducted under a dissecting or surgical microscope. The cornea of the right eye was exposed using an eyelid speculum. The central corneal area was appropriately marked as considered necessary by the surgeon. In the right eye of each animal, one 9.0 silk suture was placed intrastromally, approximately 1 mm from the limbus with 2 stromal incursions. The outer point of suture placement was chosen near the limbus (1-2 mm), and the inner suture point was chosen near the corneal center, equidistant from the limbus, to obtain standardized angiogenic responses. The left eye remained untreated.

The study design is shown below in Table 7:

TABLE 7

| Dose Formulation | Dose Strength | Dose Volume (μL/eye) | Dose Concentration (mg/mL) | Dose Route | No. of Animals Tested (males) |
|---|---|---|---|---|---|
| Suspension Vehicle | 0 | 35 | 0 | Topical | 6 |
| Avastin (active control) | 5 mg/eye | 200 | 25 | Subconjunctival | 6 |
| Axitinib[1] | 0.3% | 35 | 3 | Topical | 6 |
| Nintedanib Ethanesulfonate[1] | 0.3% | 35 | 3 | Topical | 6 |
| Sorafenib Tosylate[1] | 0.3% | 35 | 3 | Topical | 6 |

[1]Formulations were liquid microsuspensions

Dose formulations were administered by subconjunctival injection to the sutured right eye of each animal of the Avastin control group (5 mg) on Days 1 and 7, at a dose volume of 200 μL/dose immediately post suture placement. Dose formulations were given three times daily (TID) for the group administered with suspension vehicle, 0.3% Axitinib, 0.3% Nintedanib Ethanesulfonate, or 0.3% Sorafenib Tosylate for a duration of 14 days. Dose formulations were administered 6 hours apart±30 minutes by topical ocular instillation (onto the superior corneal surface) to the right eye using a calibrated positive displacement micropipette, to ensure contact with the conjunctiva. The dosing volume was one 35 μL drop per dose. After the dose was administered, the upper and lower eyelids were gently held together to prevent the loss of material and to distribute the dose across the eye.

Ocular imaging and neovascularization assessments were performed once pre-treatment, and also once on Days 7 and 14. A pre-anesthetic cocktail of Ketamine (15 mg/kg) and Dexmedetomidine (0.25 mg/kg) was administered subcutaneously, and the animals were maintained with isoflurane/oxygen mix prior to and during the procedure. Still images of the cornea were taken from both eyes (from the center of each eye, nasally and temporally). Images were evaluated qualitatively and quantitatively to assess the degree of corneal neovascularization (CNV), and to determine the area affected by CNV. The length of the vessel incursion was measured from the limbus to the distal end of the encroaching CNV using a digital micrometer (in millimeters) for each selected image. Qualitative assessments included the percentage estimate of involved corneal circumference (using multiple images as necessary), and vessel branching.

Figure 1B:
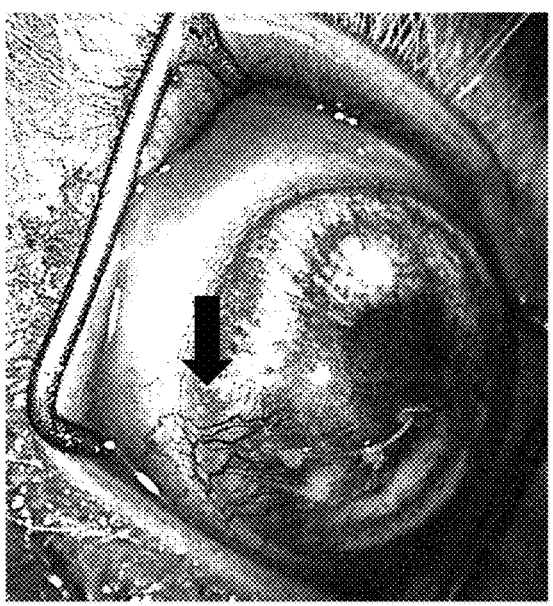
Figure 2A:
FIGS. 2A and 2B show representative photographic images of corneal neovascularization in a New Zealand white rabbit model of cornea suture-induced neovascularization upon treatment with Avastin; Avastin was administered by subconjunctival injection to the sutured eye on day 1 and day 7 post-suture placement.
Figure 2B:
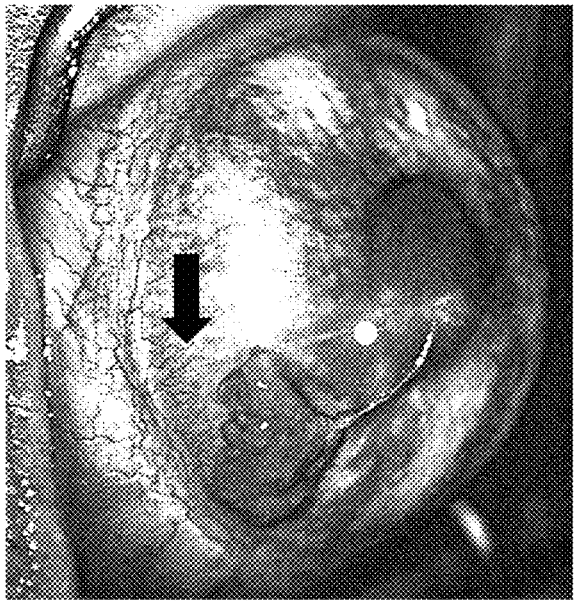

CNV was noted on Days 7 and 14 in the right eyes of animals given the suspension vehicle averaging 1 to 2.7 mm in length and affecting up to 50% of the corneal circumference, with slight to moderate branching of the vessels (see FIGS. 1A and 1B). In contrast, minimal to no CNV was noted in some animals given 5 mg Avastin/eye (see FIGS. 2A and 2B). Notably, animals treated with Avastin were observed to have minimal CNV on Day 14 (~0.5 to 1.1 mm), encompassing between 20 to 30% of the corneal circumference (FIG. 2B).

Figure 3A:
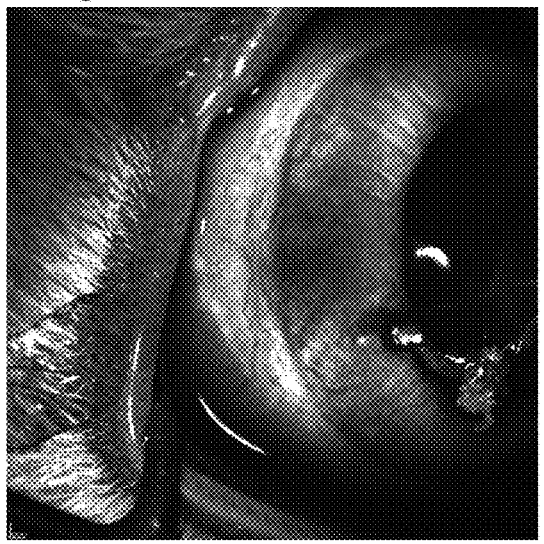
FIGS. 3A and 3B show representative photographic images of corneal neovascularization in a New Zealand white rabbit model of cornea suture-induced neovascularization upon treatment with 0.3% Axitinib administered three times daily for a duration of 14 days.
Figure 3B:
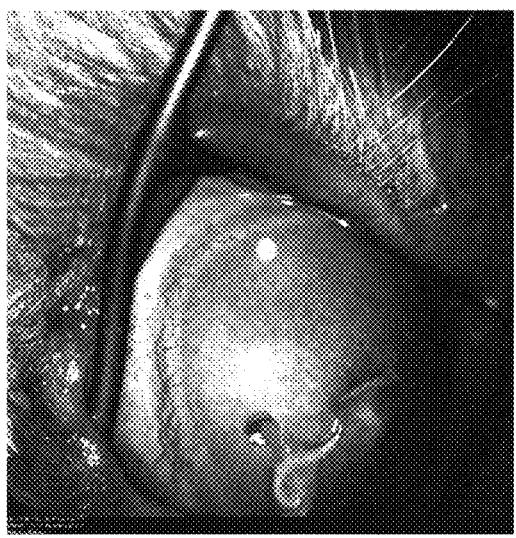
Figure 4A:
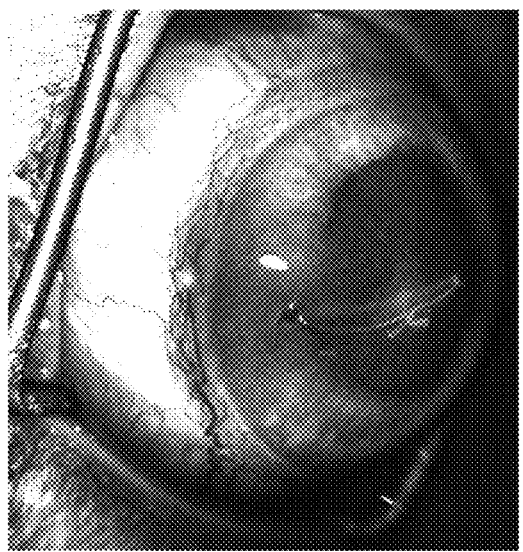
FIGS. 4A and 4B show representative photographic images of corneal neovascularization in a New Zealand white rabbit model of cornea suture-induced neovascularization upon treatment with 0.3% Nintedanib Ethanesulfonate administered three times daily for a duration of 14 days.
Figure 4B:
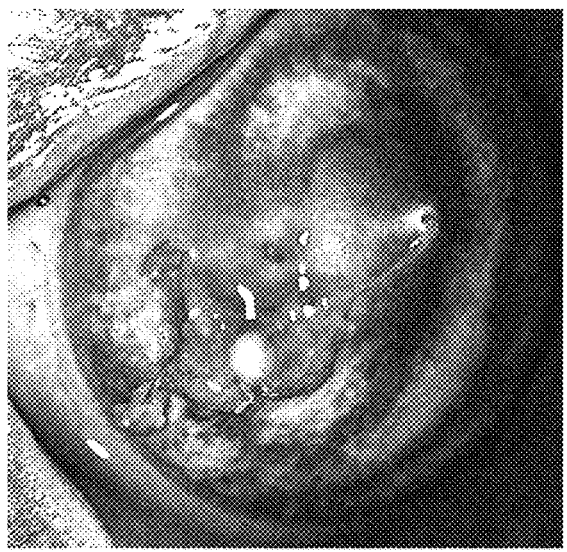
Figure 5A:
FIGS. 5A and 5B show representative photographic images of corneal neovascularization in a New Zealand white rabbit model of cornea suture-induced neovascularization upon treatment with 0.3% Sorafenib administered three times daily for a duration of 14 days.
Figure 5B:
Figure 6:
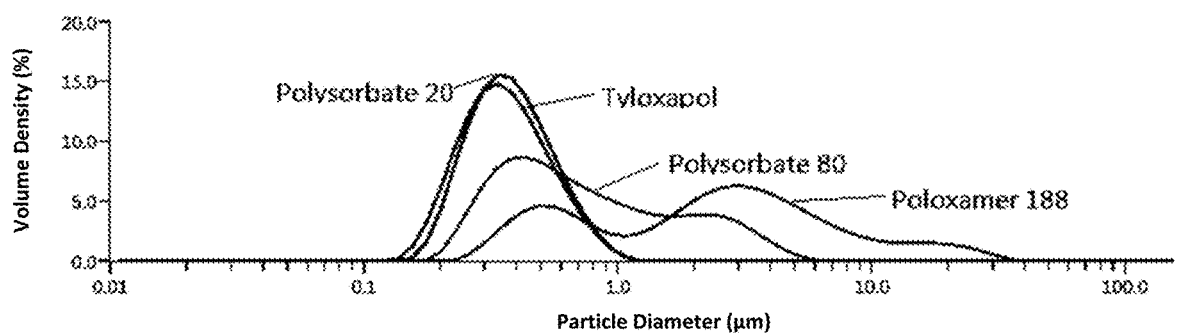
FIG. 6 is a distribution diagram that shows the effect of different surfactants on the size distribution of Nintedanib particle.

On Day 7, CNV was not observed in animals given Axitinib or Nintedanib Ethanesulfonate (see FIG. 3A and FIG. 4A). In these groups, vessels were approximately 0.5 mm in length, which covered approximate 20% of the corneal circumference and had very slight to moderate vessel branching. The group treated with Nintedanib Ethanesulfonate was considered comparable to one given Avastin at Day 7. By Day 14, the vessels were characterized as sparse and no branching was observed in the group administered with Nintedanib Ethanesulfonate (FIG. 4B). At Day 15, the group given Nintedanib Ethanesulfonate was considered slightly more efficacious compared to the one given Avastin when comparing vessel length, surface area and vessel branching. Slight corneal neovascularization was observed for animals treated with Sorafenib Tosylate on both Day 7 and Day 14 (FIG. 5A and FIG. 5B) compared with the Avastin control group, with CNV length and area increasing by Day 14. The results are also summarized below in Table 8.

TABLE 8

Summary of Corneal Neovascularization (CNV) Assessments

| Dose Formulation | CNV Length (mm) | | | CNV Area (~%) | | | CNV Branching[a] | | |
|---|---|---|---|---|---|---|---|---|---|
| | Pre 6 eyes | Day 7 6 eyes | Day 14 6 eyes | Pre 6 eyes | Day 7 6 eyes | Day 14 6 eyes | Pre 6 eyes | Day 7 6 eyes | Day 14 6 eyes |
| Suspension Vehicle | 0 | 1.07 | 2.66 | 0 | 28 | 19 | 0 | 2 | 3 |
| Avastin | 0 | 0 | 0.45 | 0 | 0 | 13 | 0 | 0 | 1 |
| 0.3% Axitinib | 0 | 0.21 | 0.25 | 0 | 0 | 8 | 0 | 0 | 1 |
| 0.3% Nintedanib Ethanesulfonate | 0 | 0 | 0.17 | 0 | 0 | 8 | 0 | 0 | 0 |
| 0.3% Sorafenib Tosylate | 0 | 0.59 | 1.77 | 0 | 18 | 32 | 0 | 1 | 2 |

[a]0 = none, 1 = very slight; 2 = slight; 3 = moderate; 4 = severe.

Over the course of the study, no treatment-related clinical signs were observed. Few ocular-related clinical signs were observed, such as eye discharge, partially closed eyes, and redness, but the observation of these instances appeared to be sporadic with no particular relation to the treatment.

The results of the above study demonstrate that ophthalmic suspension formulations containing Nintedanib Ethanesulfonate and Axitinib were both well-tolerated and efficacious in preventing or slowing CNV progression. The results also demonstrate that Nintedanib Ethanesulfonate was more efficacious, or at least comparable to Avastin in preventing or slowing CNV progression.

Example 5: Preparation of Ophthalmic Nanosuspensions Containing Nintedanib

Ophthalmic formulations in the form of liquid suspensions containing nanoparticles of Nintedanib were prepared.

Nintedanib (4.0 g) was dispersed and mixed by stirring in 200 ml 0.2% Tyloxapol solution at the room temperature. Next, the mixture of Nintedanib and Tyloxapol was milled in the 160 mL chamber of a NETZSCH® MINICER along with 200 μm zirconium oxide grinding beads. The milling speed and time was adjusted to alter certain properties of the formulation composition, such as particle size distribution. An exemplary speed and time used was 3000 rpm for 20 minutes. Following milling, the particle size distribution of the Nintedanib particles was evaluated. The particle size distribution and composition of an exemplary Nintedanib nanosuspension made according to the ball-milling process described above is shown in Table 9.

TABLE 9

1% Nintedanib Ophthalmic Nanosuspension

| Ingredient | Value |
| --- | --- |
| Nintedanib | 1% |
| Tyloxapol | 0.1% |
| EDTA•2Na | 0.01% |
| NaCl | 0.25% |
| BAK | 0.005% |
| Suspending agent | 1% HPMC |
| Potassium Phosphate buffer (10 mM) | pH 6.5 |
| Milling Speed and Time | 3000 rpm 20 min |
| D10/50/90(μm) | 0.239/0.364/0.575 |

Chemical Stability Testing

Chemical stability as well as formulation stability of nanosuspensions are important to maintain formulation characteristics and the desired pharmacological effects. The nanosuspensions were monitored at varying storage conditions, including different storage times and storage temperatures. In particular, the nanosuspensions were tested after 20 days and 30 days after storage at room temperature, 40° C., or 60° C. Some impurities were detected in all samples tested, after storage for 20 days and 30 days at room temperature, 40° C. and 60° C. similar to the initial test value.

Effect of Surfactants on Particle Size

Various surfactants including Tween 80, Tween 20, Poloxamer 188 (Pluronic® F-68), and Tyloxapol were also tested for their wetting ability in the ball-milling process. According to the results shown in Table 10, including Tyloxapol in the nanosuspension reduces the $D_{90}$ particle size down into the nanometer range, i.e., below 1 μm, as compared to the other surfactants tested in which the $D_{90}$ particle size was greater than 1 μm. The effect of the surfactants on stability in terms of particle size of the nanosuspensions was also evaluated after storage at 20 days and 30 days at room temperature, 40° C., or 60° C. The results are shown in Table 10.

TABLE 10

| Ingredient | 1 | 2 | 3 | 4 |
| --- | --- | --- | --- | --- |
| Nintedanib | 1% | 1% | 1% | 1% |
| Surfactant | 0.1% Tween 80 | 0.1% Tween 20 | 0.1% Poloxamer | 0.1% Tyloxapol |
| EDTA•2Na | 0.01% | 0.01% | 0.01% | 0.01% |
| NaCl | 0.25% | 0.25% | 0.25% | 0.25% |
| BAK | 0.005% | 0.005% | 0.005% | 0.005% |
| Suspending agent | 1% HPMC | 1% HPMC | 1% HPMC | 1% HPMC |
| Potassium Phosphate buffer (10 mM) | pH 6.5 | pH 6.5 | pH 6.5 | pH 6.5 |

Particle size: D10/50/90 (μm)

| | | 1 | 2 | 3 | 4 |
| --- | --- | --- | --- | --- | --- |
| Initial | | 0.248/0.385/0.625 | 0.243/0.376/0.602 | 0.239/0.385/0.669 | 0.239/0.364/0.575 |
| 60° C. | 20 days | 0.262/0.455/0.860 | 0.247/0.397/0.673 | 0.242/0.378/0.657 | 0.246/0.403/0.760 |
| | 30 days | 0.261/0.456/1.11 | 0.255/0.418/0.719 | 0.232/0.380/0.674 | 0.250/0.408/0.732 |
| 40° C. | 20 days | 0.299/0.550/1.20 | 0.286/0.489/0.876 | 0.261/0.481/1.18 | 0.230/0.352/0.582 |
| | 30 days | 0.295/0.543/1.17 | 0.275/0.462/0.825 | 0.274/0.546/1.97 | 0.256/0.409/0.720 |
| RT | 20 days | 0.260/0.459/1.35 | 0.272/0.441/0.781 | 0.262/0.448/1.45 | 0.221/0.339/0.550 |
| | 30 days | 0.263/0.462/1.97 | 0.270/0.461/2.97 | 0.245/0.411/0.748 | 0.260/0.414/0.696 |

As shown in Table 10 above, formulation 4 containing Tyloxapol in particular showed little or no increase in the particle size after storage for 20 days and 30 days at all temperatures tested.

Effect of Suspending Agent on Particle Size Stability in Nanosuspensions

The effects of polymers, including carboxymethylcellulose sodium (CMC-Na 7L2P, MW 49000) and hydroxypropyl methylcellulose (HPMC E4M, MW 86000) as suspending agents, on particle size stability in nanosuspensions were evaluated. The particle size of the nanosuspensions was measured after storage for 7 days, 14 days, and 28 days at 4° C., room temperature, 40° C., and 60° C. As shown in Table 11 below, little to no increase in the particle size was found in nanosuspensions containing HPMC (Formulation 1).

TABLE 11

| Ingredient | | 1 | 2 |
|---|---|---|---|
| Nintedanib | | 0.5% | 0.5% |
| Tyloxapol | | 0.05% | 0.05% |
| EDTA•2Na | | 0.01% | 0.01% |
| NaCl | | 0.25% | 0.25% |
| BAK | | 0.005% | 0.005% |
| Mannitol | | 3.3% | 3.3% |
| Suspending agent | | 0.5% HPMC | 0.5% CMC-Na |
| Particle size: D10/50/90 (μm) | | | |
| Initial | | 0.274/0.450/0.813 | 0.254/0.418/0.930 |
| 60° C. | 7 days | 0.255/0.420/0.895 | 0.268/0.453/1.31 |
| | 14 days | 0.250/0.408/0.900 | 0.305/0.559/2.14 |
| | 28 days | 0.255/0.425/1.06 | 0.291/0.531/2.33 |
| 40° C. | 14 days | 0.249/0.391/0.672 | 0.282/0.493/1.26 |
| | 28 days | 0.247/0.388/0.670 | 0.294/0.506/1.67 |
| RT | 14 days | 0.256/0.408/0.709 | 0.280/0.480/1.08 |
| | 30 days | 0.254/0.421/1.04 | 0.303/0.582/2.80 |
| 4° C. | 30 days | 0.246/0.385/0.667 | 0.282/0.482/1.12 |

Effect of pH on Particle Size Stability in Nanosuspensions

Aqueous solubility of Nintedanib varies with the pH value of the formulation, which can lead to subsequent changes in particle size. Therefore, the particle size stability of nanosuspensions with varying pH values was evaluated. The pH of the formulation was adjusted to the indicated value prior to measuring the particle size of the initial suspension. The results for formulations with pH values of 5.8, 6.5, 7.0, and 7.4 are reported in Table 12.

TABLE 12

| Ingredient | | 1 | 2 | 3 | 4 |
|---|---|---|---|---|---|
| Nintedanib | | 0.5% | 0.5% | 0.5% | 0.5% |
| Tyloxapol | | 0.05% | 0.05% | 0.05% | 0.05% |
| EDTA•2Na | | 0.01% | 0.01% | 0.01% | 0.01% |
| NaCl | | 0.25% | 0.25% | 0.25% | 0.25% |
| BAK | | 0.005% | 0.005% | 0.005% | 0.005% |
| Glycerol | | 2.5% | 2.5% | 2.5% | 2.5% |
| Suspending agent | | 0.5% HPMC | 0.5% HPMC | 0.5% HPMC | 0.5% HPMC |
| Potassium Phosphate buffer | | pH 5.8 | pH 6.5 | pH 7.0 | pH 7.4 |
| Soluble nintedanib concentration (μg/ml) | | 17.68 | 7.13 | 3.45 | 2.24 |
| Particle size: D10/50/90 (μm) | | | | | |
| Initial | | 0.274/0.450/0.813 | | | |
| 60° C. | 7 days | 0.334/0.822/256 | 0.254/0.421/1.02 | 0.253/0.415/0.928 | 0.268/0.433/0.928 |
| | 14 days | 0.297/0.510/225 | 0.257/0.429/1.03 | 0.283/0.467/0.955 | 0.254/0.418/0.957 |
| | 28 days | 0.267/0.449/1.34 | 0.258/0.431/1.05 | 0.258/0.424/0.988 | 0.261/0.441/1.23 |
| 40° C. | 14 days | 0.458/4.73/760 | 0.270/0.442/0.786 | 0.274/0.453/0.820 | 0.260/0.419/0.743 |
| | 28 days | 0.547/4.99/14.9 | 0.287/0.499/0.915 | a | 0.290/0.507/0.930 |
| 25° C. | 14 days | 0.564/5.19/91.4 | a | 0.253/0.402/0.709 | 0.272/0.443/2.17 |
| | 28 days | 0.796/6.45/21.3 | 0.256/0.409/0.720 | 0.265/0.416/0.695 | 0.280/0.513/3.91 |
| 4° C. | 14 days | 2.37/8.67/17.1 | 0.258/0.415/0.802 | 0.253/0.405/0.730 | 0.267/0.430/0.749 |
| | 28 days | 1.99/8.18/15.4 | 0.256/0.422/2.97 | 0.250/0.394/0.679 | 0.247/0.390/0.680 | a = abnormal data

The results show that at pH values higher than 5.8, such as pH 6.5, 7.0, and 7.4, the particle size remained relatively stable after 28 days.

Homogeneity of Nanosuspensions

To determine the homogeneity of nanosuspensions, nintedanib nanosuspensions containing various surfactants or at different pH as listed in Table 13 below were allowed to sit for 1 hour, followed by shaking 10 times by hand (amplitude: 10 cm). After shaking, samples were taken from top, middle, and bottom parts of the nanosuspensions and analyzed for Nintedanib content. The results, reported in Table 13 as "Homogeneity at 1 Hour," showed good suspension homogeneity after re-suspension.

TABLE 13

| Ingredient | 1 | 2 | 3 |
|---|---|---|---|
| Nintedanib | 1% | 1% | 1% |
| Surfactant | 0.3% Tween 80 | 0.1% Tyloxapol | 0.1% Tyloxapol |
| EDTA•2Na | 0.01% | 0.01% | 0.01% |
| NaCl | 0.75% | 0.75% | 0.75% |
| BAK | 0.005% | 0.005% | 0.005% |
| Suspending agent | 0.5% HPMC | 0.5% HPMC | 0.5% HPMC |
| Potassium Phosphate Buffer (10 mM) | pH 7.0 | pH 6.5 | pH 7.0 |
| Homogeneity at 1 Hour | | | |
| Average Nintedanib conc. (%) | 0.857 | 1.05 | 1.06 |
| RSD % | 0.1 | 0.1 | 0.7 |

While the invention has been described in detail, and with reference to specific embodiments thereof, it will be apparent to one of ordinary skill in the art that various changes and modifications can be made therein without departing from the spirit and scope of the invention.

We claim:

1. An ophthalmic formulation, wherein the ophthalmic formulation is an aqueous suspension comprising:

(i) a therapeutically effective amount of particles comprising nintedanib, or a pharmaceutically acceptable salt thereof; and (ii) at least one pharmaceutically acceptable excipient comprising about 0.01% to 0.3% (w/v) of tyloxapol.

2. The ophthalmic formulation of claim 1, wherein the ophthalmic formulation is an aqueous nanosuspension comprising nanoparticles comprising nintedanib, or a pharmaceutically acceptable salt thereof.

3. The ophthalmic formulation of claim 1, wherein the ophthalmic formulation is an aqueous nanosuspension comprising nanoparticles comprising nintedanib, or a pharmaceutically acceptable salt thereof.

4. The ophthalmic formulation of claim 2, wherein the nanoparticles have a $D_{90}$ particle size of less than 1.5 µm.

5. The ophthalmic formulation of claim 1, wherein at least one pharmaceutically acceptable excipient further comprises a viscosity regulator selected from the group consisting of hydroxypropyl methylcellulose (HPMC), carboxymethylcellulose (CMC), hydroxypropylcellulose (HPC), methylcellulose (MC), hydroxyethylcellulose (HEC), carbomer, polycarbophil, polyoxyethylene glycol (PEG), hyaluronic acid (HA), polyvinylpyrrolidone (PVP), polyvinyl alcohol (PVA) and a mixture thereof.

6. The ophthalmic formulation of claim 1, wherein the aqueous suspension comprises about 0.01% to 10% (w/v) of particles comprising nintedanib, or a pharmaceutically acceptable salt thereof.

7. The ophthalmic formulation of claim 6, wherein the aqueous suspension is an aqueous nanosuspension comprising nanoparticles having a $D_{90}$ particle size of less than 1.5 µm and a $D_{50}$ particle size of less than 1 µm.

8. The ophthalmic formulation of claim 1, wherein the aqueous suspension has a pH of 6.5 to 7.4.

9. A method of treating dry eye disease in a subject in need thereof, the method comprising administering to the subject an ophthalmic formulation in the form of an aqueous suspension comprising a therapeutically effective amount of particles comprising nintedanib, or a pharmaceutically acceptable salt thereof, and at least one pharmaceutically acceptable excipient comprising about 0.01% to 0.3% (w/v) of tyloxapol.

10. The method of claim 9, wherein the at least one pharmaceutically acceptable excipient further comprises a viscosity regulator selected from the group consisting of hydroxypropyl methylcellulose (HMPC), carboxymethylcellulose (CMC), hydroxypropylcellulose (HPC), methylcellulose (MC), hydroxyethylcellulose (HEC), carbomer, polycarbophil, polyoxyethylene glycol (PEG), hyaluronic acid (HA), polyvinylpyrrolidone (PVP), polyvinyl alcohol (PVA) and a mixture thereof.

11. The method of claim 10, wherein the aqueous suspension is an aqueous nanosuspension comprising about 0.01% to 10% (w/v) of particles comprising nintedanib.

12. A method of treating a surface ocular disease in a subject in need thereof, the method comprising administering to the subject an ophthalmic formulation in the form of an aqueous suspension comprising a therapeutically effective amount of particles comprising nintedanib, or a pharmaceutically acceptable salt thereof, and at least one pharmaceutically acceptable excipient comprising about 0.01% to 0.3% (w/v) of tyloxapol.

13. The method of claim 12, wherein the aqueous suspension is an aqueous nanosuspension comprising about 0.01% to 10% (w/v) of particles comprising nintedanib.

14. The method of claim 13, wherein the aqueous suspension comprises about 0.01% to 10% (w/v) nintedanib particles or particles of a pharmaceutically acceptable salt thereof and about 0.1% to 1.0% (w/v) of a viscosity regulator.

15. The method of claim 13, wherein the aqueous suspension is an aqueous nanosuspension comprising nintedanib nanoparticles having a $D_{90}$ particle size of less than 1.5 µm and a $D_{50}$ particle size of less than 1 µm.

\* \* \* \* \*